(12) United States Patent  
Kobayashi et al.

(10) Patent No.: US 8,222,177 B2  
(45) Date of Patent: Jul. 17, 2012

(54) CATALYST AND REACTION PROCESS

(75) Inventors: Shu Kobayashi, Tokyo (JP); Magno Agostinho, Serra de Santo Antonio (PT); Uwe Schneider, Tokyo (JP); Miyuki Yamaguchi, Tokyo (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 0 days.

(21) Appl. No.: 12/865,053

(22) PCT Filed: Jan. 28, 2009

(86) PCT No.: PCT/JP2009/051322
§ 371 (c)(1),
(2), (4) Date: Nov. 18, 2010

(87) PCT Pub. No.: WO2009/096409
PCT Pub. Date: Aug. 6, 2009

(65) Prior Publication Data
US 2011/0054190 A1    Mar. 3, 2011

(30) Foreign Application Priority Data
Jan. 28, 2008   (JP) ................................ 2008-015906

(51) Int. Cl.
*B01J 31/16*   (2006.01)
*C07C 311/15*   (2006.01)
(52) U.S. Cl. ......................................... 502/150; 564/83
(58) Field of Classification Search ................. 502/150; 564/83
See application file for complete search history.

(56) References Cited

OTHER PUBLICATIONS

So-Young Park, et al., "Catalytic aysmmetric Michael reactions of dibenzyl malonate to α,β-unsaturated N-acylpyrroles using a La (O-iPr)$_3$/Ph-linked-BINOL complex", Tetrahedron Letters, vol. 48, 2007, pp. 2815-2818.
Chao Chen, et al., "Preparation and application of chiral spiro nitrogen-containing ligands for cobalt-catalyzed asymmetric Michael addition", Tetrahedron:Asymmetry, vol. 17, 2006, pp. 2761-2767.
G. Kumaraswamy, et al., "Synthesis of 6,6'-and 6-MeO-PEG-BINOL-Ca soluble polymer bound ligands and their application in asymmetric Michael and epoxidation reactions", Journal of Molecular Catalysis A: Chemical, vol. 230, 2005, pp. 59-67.
S. Velmathi, et al., "Novel heterobimetallic catalysts for asymmetric Michael reactions", Tetrahedron: Asymmetry, vol. 14, 2003, pp. 113-117.
Venkatachalam Annamalai, et al., "Catalysis of the Michael Addition Reaction by Late Transition Metal Complexes of BINOL-Derived Salens", J. Org. Chem., vol. 68, 2003, pp. 1973-1981.

Youjun Xu, et al., "A practical large-scale systhesis of enantiomerically pure 3-[bis(methoxycarbonyl)methyl]cyclohexanone via catalytic asymmetric Michael reaction", Tetrahedron, vol. 58, 2002, pp. 2585-2588.
G. Kumaraswamy, et al., "Calcium-BINOL: a novel and efficient catalyst for asymmetric Michael reactions", Tetrahedron Letters, vol. 42, 2001, pp. 8515-8517.
Yun Sik Kim, et al., "Stable, Storable, and Reusable Asymmetric Catalyst: A Novel La-linked-BINOL Complex for the Catalytic Asymmetric Michael Reaction", J. Am. Chem. Soc., vol. 122, 2000, pp. 6506-6507.
Nicole End, et al, "Synthesis of Chiral Bis(dihydrooxazolylphenyl)oxalamides, a New Class of Tetradentale Ligands for Asymmetric Catalysis", Chem. Eur. J., vol. 4, No. 5, 1998, pp. 818-824.
G. Manickam, et al., "A new $C_2$-symmetric heterobimetallic complex as a promoter for asymmetric Michael addition reactions", Tetrahedron: Asymmetry, vol. 8, No. 13, 1997, pp. 2271-2278.
Hiroaki Sasai, et al., "The First Heterobimetallic Multifunctional Asymmetric Catalyst", J. Am. Chem. Soc., vol. 117, 1995, pp. 6194-6198.
Zhiming Wang, et al., "Synthesis of new chiral ionic liquids from natural acids and their applications in enantioselective Michael addition", Tetrahedron Letters, vol. 46, 2005, pp. 4657-4660.
Takashi Ooi, et al., "Importance of Chiral Phase-Transfer Catalysts with Dual Functions in Obtaining High Enantioselectivity in the Michael Reaction of Malonates and Chalcone Derivatives", Organic Letters, vol. 7, No. 15, 2005, pp. 3195-3197.
Ravindra T. Dere, et al., "Influence of ionic liquids on the phase transfer-catalysed enantioselective Michael reaction", Tetrahedron Letters, vol. 44, 2003, pp. 5351-5353.
Dae Young Kim, et al., "Enantioselective Michael reaction of malonates and chalcones by phase-transfer catalysis using chiral quaternary ammonium salt", Tetrahedron Letters, vol. 42, 2001, 6299-6301.
Jian Wang, et al., "Organocatalytic Enantioselective Conjugate Additions to Enones", J. Am. Chem. Soc., vol. 128, 2006, pp. 12652-12653.
Kristian Rahbek Knudsen, et al., "Asymmetric organocatalytic conjugate addition of malonates to enones using a proline tetrazole catalyst", Chem. Commun., 2006, pp. 66-68.
Nis Halland, et al., "Highly Enantioselective Organocatalytic Conjugate Addition of Malonates to Acyclic α,β-Unsaturated Enones", Angew. Chem. Int. Ed., vol. 42, No. 6, 2003, pp. 661-665.
Masahiko Yamaguchi, et al.. "Asymmetric Michael Addition of Malonate Anions to Prochiral Acceptors Catalyzed by L-Proline Proline Rubidium Salt", J. Org. Chem., vol. 61, 1996, pp. 3520-3530.
Masahiko Yamaguchi, et al., "A Catalytic Enantioselective Michael Addition of a Simple Malonate to Prochiral α,β-Unsaturated Ketones and Aldehydes**", Angew. Chem. Int. Ed. Engl., vol. 32, No. 8, 1993, pp. 1176-1178.

*Primary Examiner* — Robert Havlin
(74) *Attorney, Agent, or Firm* — Oblon, Spivak, McClelland, Maier & Neustadt, L.L.P.

(57) ABSTRACT

Disclosed is a technology for enabling an efficient asymmetric Michael addition reaction which does not require a large amount of a malonic ester, while having a short reaction time. Specifically disclosed is a catalyst which is composed of $MX^2$ (wherein M is Be, Mg, Ca, Sr, Ba or Ra and X is an arbitrary group) and a compound represented by general formula [I]. [In the formula, $R^7$, $R^8$, $R^9$ and $R^{10}$ each represents a substituted cyclic group or an unsubstituted cyclic group.]

12 Claims, No Drawings

CATALYST AND REACTION PROCESS

APPLICABLE FIELD IN THE INDUSTRY

The present invention relates to a catalyst and a reaction method. The present invention relates, for example, to a technology of highly enantioselective addition reaction to an enone using a malonic ester as a nucleophile.

BACKGROUND ART

The reaction between a malonic ester and an enone is shown in the following documents.

Non-patent document 1: Park, S.-Y.; Morimoto, H.; Matsunaga, S.; Shibasaki, M. Tetrahedron Lett. 2007, 48, 2815-2818.

Non-patent document 2: Chen, C.; Zhu, S.-F.; Wu, X.-Y.; Zhou, Q.-L. Tetrahedron: Asymmetry 2006, 17, 2761-2767.

Non-patent document 3: Kumaraswamy, G.; Jena, N.; Sastry, M. N. V.; Rao, G. V.; Ankamma, K. J. Mol. Catal. A 2005, 230, 59-67.

Non-patent document 4: Velmathi, S.; Swarnalakshmi, S.; Narasimhan, S. Tetrahedron: Asymmetry 2003, 14, 113-117.

Non-patent document 5: Annamalai, V.; DiMauro, E. F.; Carroll, P. J.; Kozlowski, M. C. J. Org. Chem. 2003, 68, 1973-1981.

Non-patent document 6: Xu, Y.; Ohori, K.; Ohshima, T.; Shibasaki, M. Tetrahedron 2002, 58, 2585-2588.

Non-patent document 7: Kumaraswamy, G.; Sastry, M. N. V.; Jena, N. Tetrahedron Lett. 2001, 42, 8515-8517.

Non-patent document 8: Kim, Y. S.; Matsunaga, S.; Das, J.; Sekine, A.; Ohshima, T.; Shibasaki, M. J. Am. Chem. Soc. 2000, 122, 6506-6507.

Non-patent document 9: End, N.; Macko, L.; Zehnder, M.; Pfaltz, A. Chem. Eur. J. 1998, 4, 818-824.

Non-patent document 10: Manickam, G.; Sundararajan, G. Tetrahedron: Asymmetry 1997, 8, 2271-2278.

Non-patent document 11: Sasai, H.; Arai, T.; Satow, Y.; Houk, K. N.; Shibasaki, M. J. Am. Chem. Soc. 1995, 117, 6194-8.

Non-patent document 12: Wang, Z.; Wang, Q.; Zhang, Y.; Bao, W. Tetrahedron Lett. 2005, 46, 4657-4660.

Non-patent document 13: Ooi, T.; Ohara, D.; Fukumoto, K.; Maruoka, K. Org. Lett. 2005, 7, 3195-3197.

Non-patent document 14: Dere, R. T.; Pal, R. R.; Patil, P. S.; Salunkhe, M. M. Tetrahedron Lett. 2003, 44, 5351-5353.

Non-patent document 15: Kim, D. Y.; Huh, S. C.; Kim, S. M. Tetrahedron Lett. 2001, 42, 6299-6301.

Non-patent document 16: Wang, J.; Li, H.; Zu, L.; Jiang, W.; Xie, H.; Duan, W.; Wang, W. J. Am. Chem. Soc. 2006, 128, 12652-12653.

Non-patent document 17: Knudsen, K. R.; Mitchell, C. E. T.; Ley, S. V. Chem. Commun. 2006, 66-68.

Non-patent document 18: Halland, N.; Aburel, P. S.; Jorgensen, K. A. Angew. Chem., Int. Ed. 2003, 42, 661-665.

Non-patent document 19: Yamaguchi, M.; Shiraishi, T.; Hirama, M. J. Org. Chem. 1996, 61, 3520-30.

Non-patent document 20: Yamaguchi, M.; Shiraishi, T.; Hirama, M. Angew. Chem., Int. Ed. 1993, 32, 1176-8.

DISCLOSURE OF THE INVENTION

[Problems to be Solved by the Invention]

Conventionally, an asymmetric Michael addition reaction between a malonic ester and an enone requires a large volume of a malonic ester so as to gain a high yield. Yet, a reaction time thereof is long. For this, the prior art is poor in efficiency.

Thus, a task that the present invention is to solve, that is, an object of the present invention is to provide, for example, a technology for enabling an efficient asymmetric Michael addition reaction that does not require a large amount of a malonic ester, while having a short reaction time.

[Means for Solving the Problem]

The foregoing problems are solved by a catalyst configured using $MX_2$ (wherein M is Be, Mg, Ca, Sr, Ba or Ra and X is an arbitrary group) and a compound represented by the following general formula [I].

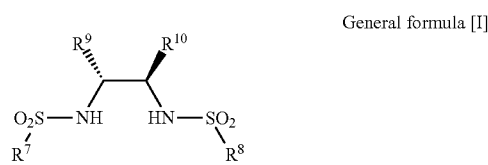

General formula [I]

[$R^7$, $R^8$, $R^9$, and $R^{10}$ each represents a substituted cyclic group or an unsubstituted cyclic group. There are two cases for $R^9$ and $R^{10}$, i.e. the case that they form a ring and the case that they do not form a ring.]

And, the foregoing problems are solved by the above-mentioned catalyst that is characterized in that the foregoing X is an alkoxide group. Among others, the foregoing problems are solved by the above-mentioned catalyst that is characterized in that the foregoing $MX_2$ is $M(OR^5)_2$ (M is Mg, Ca, Sr or Ba. $R^5$ is an alkyl group). More preferably, the foregoing problems are solved by the above-mentioned catalyst that is characterized in that the foregoing $MX_2$ is $M(OR^5)_2$ (M is Ca, Sr or Ba. $R^5$ is an alkyl group having a carbon number of 1 to 10). In particular, the foregoing problems are solved by the above-mentioned catalyst that is characterized in that the foregoing $MX_2$ is $Sr(OR^5)_2$ ($R^5$ is an alkyl group having a carbon number of 1 to 10).

Further, the foregoing problems are solved by the above-mentioned catalyst that is characterized in that the foregoing X is an amide group. In particular, the foregoing problems are solved by the above-mentioned catalyst that is characterized in that the foregoing X is hexamethyldisilazide (HMDS).

Further, the foregoing problems are solved by the above-mentioned catalyst that is characterized in that the foregoing cyclic group of the foregoing general formula [I] is an aromatic group.

Further, the foregoing problems are solved by the above-mentioned catalyst that is characterized in that the compound represented by the foregoing general formula [I] and M of the foregoing compound $MX_2$ are coordinate-bonded to each other.

The above-mentioned catalyst is a catalyst that is used for a reaction between a compound represented by the following general formula [II] and a compound represented by the following general formula [III].

General formula [II]

-continued

General formula [III]

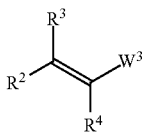

Each of the foregoing $R^1$, $R^2$, $R^3$, and $R^4$ is an arbitrary substituent. Preferably, it is an H group or a hydrocarbon group.

Each of the foregoing $W^1$, $W^2$, and $W^3$ is an electron-withdrawing group. Preferably, it is an ester group or a carbonyl group.

The compound represented by the foregoing general formula [II] is, particularly, a dicarboxylate ester. Among others, it is a malonic ester.

The compound represented by the foregoing general formula [III] is, particularly, an enone.

Further, the foregoing problems are solved by a reaction method that is characterized in reacting the compound represented by the foregoing general formula [II] with the compound represented by the foregoing general formula [III] in the presence of the foregoing catalyst.

A molecular sieve is preferably added to a solution of the foregoing reaction. Further, an aromatic hydrocarbon solvent is preferably used as a solvent of the foregoing reaction.

And, a compound represented by the following general formula [IV] is obtained with the above-mentioned reaction.

General formula [IV]

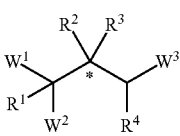

AN ADVANTAGEOUS EFFECT OF THE INVENTION

A large amount of the compound of the foregoing general formula [II] such as a malonic ester is not required in the asymmetric Michael addition reaction between the compound of the foregoing general formula [II] (for example, a dicarboxylate ester such as a malonic ester) and the compound of the foregoing general formula [III] (for example, an enone).

And, the reaction time was shortened.

That is, the compound of the foregoing general formula [IV] was efficiently obtained.

BEST MODE FOR CARRYING OUT THE INVENTION

The present invention relates to a catalyst. In particularly, the present invention relates a catalyst that is used for the reaction between the compound represented by the foregoing general formula [II] and the compound represented by the foregoing general formula [III]. Each of the foregoing $R^1$, $R^2$, $R^3$, and $R^4$ of the foregoing general formula [II] and general formula [III] is an arbitrary substituent. In particular, it is an H group or a hydrocarbon group. Each of the foregoing $W^1$, $W^2$, and $W^3$ of the foregoing general formula [II] and general formula [III] is an electron-withdrawing group. For example, it is an electron-withdrawing group such as an ester group, a carboxyl group, a carbonyl group, a nitrile group, a nitro group, and a hydroxyl group. The particularly preferable electron-withdrawing group is an ester group and a carbonyl group. The preferable compound of the foregoing general formula [II] is a dicarboxylate ester. Among others, it is a malonic ester. In particular, it is a malonic ester represented by $R^aOOCCH_2COOR^b$ (each of $R^a$ and $R^b$ is a hydrocarbon group. In particular, it is a hydrocarbon group having a carbon number of 1 to 10. For example, it is an alkyl group having a carbon number of 1 to 6.) The preferable compound of the foregoing general formula [III] is an enone.

The catalyst of the present invention is configured using a compound A and a compound B. The compound A is a compound represented by $MX_2$ (M is a member selected from a group of alkaline earth metals. X is an arbitrary group.) The compound B is a compound represented by the foregoing general formula [I]. The alkaline earth metal is Be, Mg, Ca, Sr, Ba, or Ra. The preferable alkaline earth metal is Mg, Ca, Sr, or Ba. The particularly preferable alkaline earth metal is Ca, Sr, or Ba. Among others, it is Sr. Any group is acceptable as far as the group X bonded with the alkaline earth metal is concerned. The preferable group, out of the group X, is an alkoxide group. For example, it is an alkoxide group having a carbon number of 1 to 10. More preferably, it is an alkoxide group having a carbon number of 1 to 6. For example, it is a propoxide group such as i-propoxide group, or a butoxide group such as a tert-butoxide group. An amide group is also a preferable group instead of the foregoing alkoxide group. For example, hexamethyldisilazide (HMDS) is a particularly preferable group similarly to the propoxide group. That is, isopropanol is generated within a reaction system when strontium isopropoxide is used as the foregoing $MX_2$. On the other hand, hexamethyldisilazane (base) is generated within a reaction system when strontium hexamethyldisilazide is used as the foregoing $MX_2$. Thus, the reaction progresses without the base added. Therefore, the above reaction is applicable to other reaction requiring the base. Further, using hexamethyldisilazide allowed the reaction to progress at a high yield and highly enantioselectively, similarly to the case of using isopropoxide. Each of $R^7$, $R^8$, $R^9$, and $R^{10}$ of the foregoing general formula [I] is a cyclic group. There are two cases for this cyclic group, i.e. the case of having a substituent and the case of not having a substituent. The preferable cyclic group is an aromatic group. For example, it is a phenyl group. Or it is a phenyl group having a substituent. Additionally, with regard to $R^9$ and $R^{10}$, there is the case that a ring is formed by $R^9$ and $R^{10}$. Needless to say, there is case that no ring is formed. And, the catalyst of the present invention is configured using the foregoing compound A and the foregoing compound B. For example, mixing the foregoing compound A and the foregoing compound B allows the catalyst of the present invention to be configured. For example, the catalyst (the catalysts of the present invention) assuming a structure in which the alkaline earth metal has been coordinate-bonded to an asymmetric ligand represented by the foregoing general formula [I] is configured. A preferable mixture ratio of the foregoing compound A and the foregoing compound B is A:B=1:1 to 2 (mole ratio).

The present invention also relates to a reaction method. In particularly, the present invention relates a reaction method of obtaining the compound represented by the foregoing general formula [IV]. That is, the method of the present invention is a method of reacting the compound represented by the foregoing general formula [II] with the compound represented by the foregoing general formula [III] in the presence of the foregoing catalyst of the present invention. An amount of the catalyst is 0.01 to 20 parts by mass to 100 parts by mass of a substrate. In particular, it is 0.5 to 10 parts by mass. The reaction is conducted at temperature of 0° C. to room temperature. Molecular sieve is preferably added to a solution of this reaction. Further, an aromatic hydrocarbon solvent such as toluene, xylene, and benzene, is preferably used as a solvent.

Hereinafter, the present invention will be explained more specifically.

As the compound A represented by $MX_2$, calcium isopropoxide $(Ca(O-i-Pr)_2)$, strontium isopropoxide $(Sr(O-i-Pr)_2)$, barium butoxide $(Ba(O-t-Bu)_2)$, magnesium butoxide $(Mg(O-t-Bu)_2)$ were used.

$Ca(O-i-Pr)_2$ was procured from Sigma-Aldrich Company. $Sr(O-i-Pr)_2$ and $Ba(O-t-Bu)_2$ were procured from JAPAN PURE CHEMICAL CO., LTD. $Mg(O-t-Bu)_2$ was procured from Alfa Aesar Company.

An asymmetric ligand III represented by the general formula [I] in accordance with the present invention was synthesized with the method described in the document (Evans, D. A.; Nelson, S. G. J. Am. Chem. Soc. 1997, 119, 6452 to 6453). An asymmetric ligand I, being a comparative example, was synthesized with the method described in the document (Lowenthal, R, E.; Abiko, A.; Masamune, S. Tetrahedron Lett. 1990, 31, 6005-8). An asymmetric ligand II, being a comparative example, was synthesized with the method described in the document (Hilgraf, R.; Pfaltz, A. Adv. Synth. Catal. 2005, 347, 61-77).

A malonic ester 1a (where R is Me), a malonic ester 1b (where R is Et), a malonic ester 1c (where R is n-Pr), a malonic ester 1e (where R is n-Bu), and a malonic ester 1f (where R is Bn (benzyl group)) shown in Table 2 were procured from TOKYO CHEMICAL INDUSTRY CO., LTD. (TCI). A malonic ester 1d (where R is i-Pr) was procured from Wako Pure Chemical industries, LTD.

α,β-unsaturated carbonyl compounds 2a, 2b, 2c, 2d, 2e, 2f, 2g, 2h, 2i, 2j, 2k, 2l, 2m, 2n, 2o, 2p, 2q, 2t, and 2u shown in Table 3 were procured from TCI, Sigma-Aldrich Company, Alfa Aesar Company, Acros Company, and Wako Pure Chemical industries, LTD. An O-unsaturated carbonyl compound 2r shown in Table 3 was synthesized with the method described in the document (Bhagat, S.; Sharma, R.; Sawant, D. M.; Sharma, L.; Chakraborti, A. K. J. Mol. Catal. A: Chem. 2006, 244, 20-24). An α,β-unsaturated carbonyl compound 2s shown in Table 3 was synthesized with the method described in the document (Evans, D. A.; Borg, G; Scheidt, K. A. Angew. Chem., Int. Ed. 2002, 41, 3188-3191). Additionally, the above-mentioned α,β-unsaturated carbonyl compounds 2b to 2u are equivalent to entries 1 to 20 of Table 3, respectively.

Molecular sieves (powder) were procured from Aldrich Company, and activated (200° C., <1 mmHg, 16 hours) for use.

Toluene was procured from Wako Pure Chemical industries, LTD. And, this toluene (anhydride solvent) was distilled in the presence of benzophenone and sodium.

[Asymmetric ligand III]

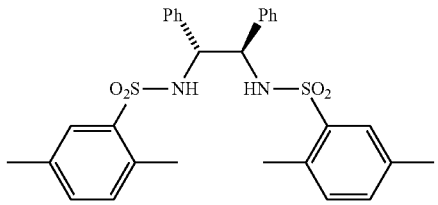

(1R,2R)-1,2-Diphenylethylene-1,2-bis(2,5-dimethylphenyl)sulfonamide:

$^1$H NMR (600.2 MHz, THF-$D_8$, TMS): δ=7.37 (s, 2H; Ar), 7.06-6.81 (m, 12H; Ar, NH), 6.72-6.67 (m, 4H; Ar), 4.43 (m, 2H, CH), 2.40 (s, 6H, $CH_3$), 2.14 (s, 6H, $CH_3$); $^{13}C$ {$^1$H} NMR (150.9 MHz, THF-D8, TMS): δ=140.0, 138.2, 136.1, 134.6, 133.2, 132.7, 130.3, 128.7, 128.2, 127.9, 63.3, 20.6, 19.7; $[\alpha]^{21}_D$=+40.27 (c=1.0 in $CHCl_3$), for the SS enantiomer of III Evans reported $[\alpha]_D$=−42 (c=0.96 in $CHCl_3$).

[Complex A]

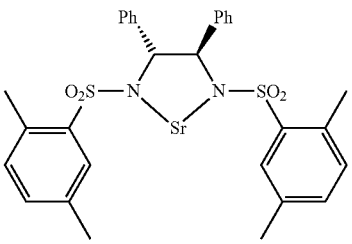

Complex A

The complex A was prepared by stirring $Sr(O-i-Pr)_2$ (0.15 mmol) in one equivalent of the asymmetric ligand III, and deuterated THF (0.75 mL) for two hours.

$^1$H NMR (600.2 MHz, THF-$D_8$, TMS): δ=7.40-6.60 (br m, 16H; Ar), 4.40 (br m, 2H; CH), 3.86-3.79 (m, 2H; CH free i-PrOH), 3.43 (d, 3JHH=3.6 Hz, 2H; OH free i-PrOH), 2.53 (br s, 6H; CH3), 1.44 (br s, 6H; $CH_3$), 1.06 (d, $J_{HH}$=6.1 Hz, 12H; $CH_3$ free i-PrOH); $^{13}C$ {$^1$H} NMR (150.9 MHz, THF-$D_8$, TMS): δ=145.6, 144.8, 134.9, 134.2, 131.6, 130.8, 129.7, 127.7, 125.9, 69.4, 63.6 (free i-PrOH), 25.9 (free i-PrOH), 21.1, 20.3.

[Complex B]

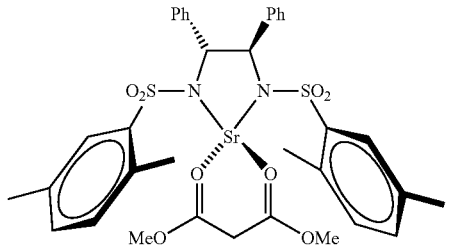

Complex B

The complex B was prepared by adding one equivalent of dimethyl malonate (1a, 17 uL) to THF (H=D) containing the complex A.

And, NMR thereof was observed in a solution state.

$^{13}C$ {$^1$H} NMR (150.9 MHz, THF-$D_8$, TMS) selected data: δ=174.6 (COO, coordinated malonate), 68.8 (NCH, ligand), 64.6 ($CH_2$, malonate), 63.6 (free i-PrOH), 49.7 ($OCH_3$, malonate), 25.9 (free i-PrOH), 20.6 ($CH_3$, ligand), 19.8 ($CH_3$, ligand).

[A method of Preparing a Crude Material]

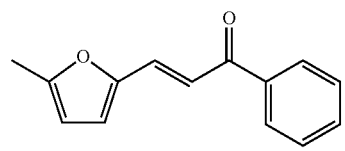

3-(5-Methylfuran-2-yl)-1-phenylprop-2-en-1-one

It was prepared with the method described in the document (Bhagat, S.; Sharma, R.; Sawant, D. M.; Sharma, L.; Chakraborti, A. K. J. Mol. Catal. A: Chem. 2006, 244, 20-24).

(Yield 63%), Yellow solid, Mp 57-61° C.: IR[cm$^{-1}$] (KBr): 1580, 1520, 1367, 1016: $^1$H NMR (600.2 MHz, CDCl$_3$, TMS): δ=8.05-8.01 (m, 2H), 7.58-7.46 (m, 4H), 7.38 (d, $J_{HH}$=15.2 Hz, 1H), 6.62 (d, $J_{HH}$=3.4 Hz, 1H), 6.13 (d, $J_{HH}$=3.4 Hz, 1H), 2.39 (s, 3H); $^{13}$C {$^1$H} NMR (150.9 MHz, CDCl$_3$, TMS): δ=189.8, 155.9, 150.3, 138.4, 132.5, 130.8, 128.5, 128.4, 118.3, 117.5, 109.4, 109.3, 14.0: ESI-HRMS (m/z) calcd. for C$_{14}$H$_{13}$O$_2$ ((M+H)$^+$): 213.0916, found: 213.0924, calcd. for C$_{14}$H$_{12}$O$_2$Na ((M+Na)$^+$): 235.0735, found: 235.0732.

2s

3-Phenyl-1-(1H-pyrrol-1-yl)prop-2-en-1-one

It was prepared with the method described in the document (Evans, D. A.; Borg, G.; Scheidt, K. A. Angew. Chem., Int. Ed. 2002, 41, 3188-3191).

White solid, Mp 101-105° C.: IR [cm$^{-1}$] (KBr): 1689, 1624, 1468, 1352: $^1$H NMR (495.1 MHz, CDCl$_3$, TMS): δ=7.99 (d, $J_{HH}$=15.5 Hz, 1H), 7.64-7.60 (m, 2H), 7.48-7.41 (m, 5H), 7.14 (d, $J_{HH}$=15.5 Hz, 1H), 6.36 (appearance of t, $J_{HH}$=2.4 Hz, 2H); $^{13}$C {$^1$H} NMR (150.9 MHz, CDCl$_3$, TMS): δ=162.9, 147.5, 134.2, 130.9, 129.0, 128.4, 119.3, 115.7, 113.4.

[A General Manipulation of the Catalytic Asymmetric Michael Reaction]

A flask with a capacity of 30 mL was heated and dried. A toluene (1.0 mL) suspension of Sr(O-i-Pr)$_2$ (0.015 mmol), the foregoing ligand III (0.018 mmol), and molecular sieves MS 4A (100 mg) were poured into this flask. And it was stirred for two hours at room temperature.

Thereafter, a toluene (1.0 mL) solution of diethyl malonate (0.36 mmol) and a toluene (1.0 mL) solution of chalcone (0.30 mmol) were sequentially added.

After confirming the finishing of the reaction by use of TLC, a saturated ammonium chloride aqueous solution NH$_4$Cl (10 mL) was added. And an organic phase was separated by adding methylene chloride (CH$_2$Cl$_2$, 10 mL), and was extracted from a water phase with methylene chloride CH$_2$Cl$_2$ (15 mL×3).

The organic phase was collected, and dried over anhydrous sodium sulfate.

After filtering and concentration under reduced pressure, the crude product was refined with a preparative thin-layer chromatography (hexane/ethyl acetate=4/1). With this, the target compound was obtained.

Enantioselectivity was determined by an HPLC analysis of the target compound.

Additionally, the above-mentioned reaction formula is shown in the following Table 1 to Table 3.

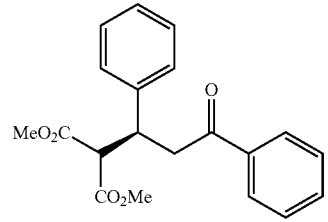

3aa

Dimethyl 2-(3-oxo-1,3-diphenylpropyl)malonate (table 2, entry 1)

It was synthesized in accordance with the above-mentioned manipulation.

Yield 65%, White solid, Mp 77-80° C.: IR [cm$^{-1}$] (KBr): 1730, 1680, 1239, 1157: $^1$H NMR (600.2 MHz, CDCl$_3$, TMS): δ=7.91-7.88 (m, 2H; Ar), 7.55-7.50 (m, 1H; Ar), 7.44-7.39 (m, 2H; Ar), 7.27-7.22 (m, 4H; Ar), 7.20-7.15 (m, 1H; Ar), 4.22-4.16 (m, 1H; CH), 3.88-3.85 (m, 1H; CH), 3.72 (s, 3H, CH$_3$), 3.56-3.46 (m, 5H; CH$_2$, CH$_3$), $^{13}$C {$^1$H} NMR (150.9 MHz, CDCl$_3$, TMS): δ=197.5, 168.7, 168.1, 140.4, 136.8, 133.1, 128.5, 128.5, 128.1 (from intensity corresponds to 2 peaks), 127.2, 57.3, 52.6, 42.3, 40.7: HPLC (Chiralpak AS-H, hexane/i-propanol=19/1, flow rate 0.5 mL/min, λ=254 nm): t$_{major}$=38.7 min, t$_{minor}$=46.3 min, ee=94%: [α]$^{21}_D$=+27.37 (c=2.0 in CHCl$_3$), literature value reported by Shibasaki[7] for the S enantiomer [α]$^{24}_D$=+25.64 (c=2.0 in CHCl$_3$, 77% ee); ESI-HRMS (m/z) calcd. for C$_{20}$H$_{20}$O$_5$Na ((M±Na)$^+$): 363.1208, found: 363.1282.

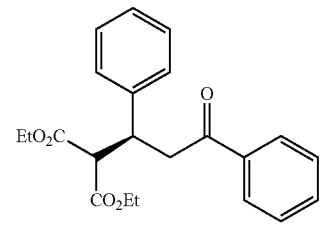

3ba

Diethyl 2-(3-oxo-1,3-diphenylpropyl)malonate (table 2, entry 2)

It was synthesized in accordance with the above-mentioned manipulation.

Yield 97%, White solid, Mp 62-66° C.: IR [cm$^{-1}$] (KBr): 1731, 1685, 1288, 1241: $^1$H NMR (600.2 MHz, CDCl$_3$, TMS): δ=7.90-7.86 (m, 2H; Ar), 7.52-7.49 (m, 1H; Ar), 7.42-7.38 (m, 2H; Ar), 7.28-7.21 (m, 4H; Ar), 7.17-7.13 (m, 1H; Ar), 4.24-4.14 (m, 3 H; CH, OCH$_2$), 3.94 (q, 3J$_{HH}$=7.1 Hz, 2H; OCH$_2$), 3.83 (d, 3J$_{HH}$=9.6 Hz, 1H; CH), ABM spin system (A=B=M=H, δ$_A$=3.54, δ$_B$=3.46, $^2$J$_{AB}$=16.6, $^3$J$_{AM}$=4.4, $^3$J$_{BM}$=9.1 Hz, 2H; CH$_2$), 1.23 (t, $^3$J$_{HH}$=7.1 Hz, 3H; CH$_3$), 1.00 (t, $^3$J$_{HH}$=7.1 Hz, 3H; CH$_3$); $^{13}$C {$^1$H} NMR (150.9 MHz, CDCl$_3$, TMS): δ=197.5, 168.4, 167.1, 140.5, 136.8, 133.0, 128.5, 128.4, 128.2, 128.1, 127.1, 61.6, 61.3, 57.6, 42.6, 40.8, 14.0, 13.8: HPLC (Chiralpak AS-H, hexane/i- propanol=19/1, flow rate 0.5 mL/min, λ=254 nm): $t_{major}$=28.1 min, $t_{minor}$=31.8 min, ee=97% $[\alpha]^{22}_D$=+19.39 (c=1.0 in CHCl$_3$), $[\alpha]^{19}_D$=+6.35 (c=2.5 in benzene), literature value reported by Koga[9] for the S enantiomer $[\alpha]^{25}_D$=+5.4 (c=2.61 in benzene, 82% ee): ESI-HRMS (m/z) calcd. for C$_{22}$H$_{24}$O$_5$Na ((M+Na)$^+$): 391.1521, found: 391.1502.

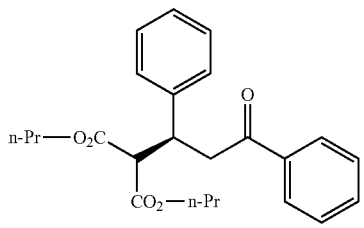

3ca

Dipropyl 2-(3-oxo-1,3-diphenylpropyl)malonate (table 2, entry 3)

It was synthesized in accordance with the above-mentioned manipulation.

Yield 92%, White solid, Mp 55-58° C.: IR [cm$^{-1}$] (KBr): 1725, 1686, 1293, 1241, 1168: $^1$H NMR (600.2 MHz, CDCl$_3$, TMS): δ=7.89-7.87 (m, 2H; Ar), 7.52-7.49 (m, 1H; Ar), 7.42-7.38 (m, 2H; Ar), 7.28-7.21 (m, 4H; Ar), 7.17-7.13 (m, 1H; Ar), 4.19 (t d, $^3J_{HH}$=4.5, $^3J_{HH}$=9.4 Hz, 1H; CH), 4.14-4.05 (m, 2H; OCH$_2$), 3.87-3.83 (m, 3H; CH, OCH$_2$), ABM spin system (A=B=M=H, δ$_A$=3.54, δ$_B$=3.47, $^2J_{AB}$=16.7, $^3J_{AM}$=4.6, $^3J_{BM}$=9.1 Hz, 2H; CH$_2$), 1.63 (appearance of sext, $^3J_{HH}$=7.1 Hz, 2H; CH$_2$CH$_3$), 1.47-1.37 (m, 2H; CH$_2$CH$_3$), 0.90 (t, $^3J_{HH}$=7.3 Hz, 3H; CH$_3$), 0.77 (t, 3J$_{HH}$=7.5 Hz, 3H; CH$_3$); $^{13}$C {$^1$H} NMR (150.9 MHz, CDCl$_3$, TMS): δ=197.6, 168.5, 167.9, 140.6, 136.9, 133.0, 128.5, 128.4, 128.2, 128.1, 127.1, 67.2, 66.9, 57.6, 42.6, 40.8, 21.8, 21.6, 10.3, 10.2: HPLC (Chiralpak AS-H, hexane/i-propanol=100/1, flow rate 0.5 mL/min, λ=254 nm): $t_{major}$=47.2 min, $t_{minor}$=52.0 min, ee=99%; $[\alpha]^{21}_D$=+24.29 (c=1.0 in CHCl$_3$); ESI-HRMS (m/z) calcd. for C$_{24}$H$_{28}$O$_5$Na ((M+Na)$^+$): 419.1834, found: 419.1865.

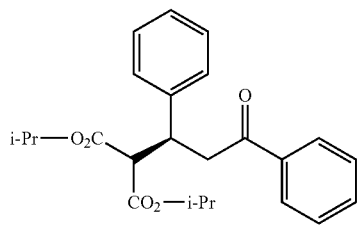

3da

Diisopropyl 2-(3-oxo-1,3-diphenylpropyl)malonate (table 2, entry 7)

It was synthesized in accordance with the above-mentioned manipulation.

Yield 83%, White solid, Mp 69-71° C.; IR [cm$^{-1}$] (KBr): 1725, 1685, 1283, 1239, 1106; $^1$H NMR (600.2 MHz, CDCl$_3$, TMS): δ=7.90-7.86 (m, 2H; Ar), 7.52-7.48 (m, 1H; Ar), 7.40 (br t, $^3J_{HH}$=7.7 Hz, 2H; Ar), 7.27-7.19 (m, 4H; Ar), 7.16-7.12 (m, 1H; Ar), 5.07 (sept, $^3J_{HH}$=6.2 Hz, 1H; CH), 4.79 (sept, $^3J_{HH}$=6.3 Hz, 1H; CH), 4.16 (t d, $^3J_{HH}$=9.7, $^3J_{HH}$=4.1 Hz, 1H; CH), 3.78 (d, $^3J_{HH}$=9.7 Hz, 1H; CH), ABM spin system (A=B=M=H, δ$_A$=3.53, δ$_B$=3.43, $^2J_{AB}$=16.5, $^3J_{AM}$=4.1, $^3J_{BM}$=9.7 Hz, 2H; CH$_2$), 1.23 (d, $^3J_{HH}$=6.3 Hz, 6H; CH$_3$), 1.04 (d, $^3J_{HH}$=6.2 Hz, 3H; CH$_3$), 0.96 (d, $^3J_{HH}$=6.2 Hz, 3H; CH$_3$); $^{13}$C {$^1$H} NMR (150.9 MHz, CDCl$_3$, TMS): δ=197.6, 167.9, 167.2, 140.5, 136.9, 133.0, 128.5, 128.4, 128.3, 128.1, 127.0, 69.2, 68.8, 57.9, 42.9, 40.7, 21.7, 21.5, 21.3, 21.3; HPLC (Chiracel OD-H, hexane/i-propanol=9/1, flow rate 0.5 mL/min, λ=254 nm): $t_{major}$=12.4 min, $t_{minor}$=13.7 min, ee=89%; $[\alpha]^{22}_D$=+21.27 (c=1.0 in CHCl$_3$); ESI-HRMS (m/z) calcd. for C$_{24}$H$_{28}$O$_5$Na ((M+Na)$^+$): 419.1834, found: 419.1898.

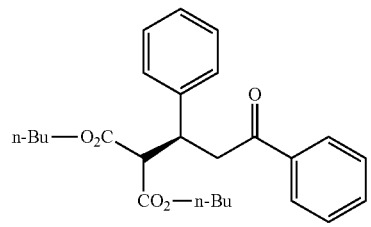

3ea

Dibutyl 2-(3-oxo-1,3-diphenylpropyl)malonate8 (table 2, entry 8)

It was synthesized in accordance with the above-mentioned manipulation.

Yield 85%, Colorless liquid; IR [cm$^{-1}$] (neat): 1733, 1687, 1254, 1223, 1158; $^1$H NMR (600.2 MHz, CDCl$_3$, TMS): δ=7.90-7.87 (m, 2H; Ar), 7.52-7.48 (m, 1H; Ar), 7.41-7.38 (m, 2H; Ar), 7.28-7.2o (m, 4H; Ar), 7.17-7.13 (m, 1H; Ar), 4.21-4.09 (m, 3H; CH, OCH$_2$), 3.92-3.84 (m, 3H; CH, OCH$_2$), ABM spin system (A=B=M=H, δ$_A$=3.54, δ$_B$=3.46, $^2J_{AB}$=16.7, $^3J_{AM}$=4.5, $^3J_{BM}$=9.3 Hz, 2H; CH$_2$), 1.61-1.55 (m, 2H; CH$_2$), 1.41-1.30 (m, 4H; CH$_2$), 1.22-1.15 (m, 2H; CH$_2$), 0.89 (t, $^3J_{HH}$=7.3 Hz, 3H; CH$_3$), 0.82 (t, $^3J_{HH}$=7.3 Hz, 3H; CH$_3$); $^{13}$C {$^1$H} NMR (150.9 MHz, CDCl$_3$, TMS): δ=197.5, 168.5, 167.8, 140.6, 136.9, 133.0, 128.5, 128.4, 128.2, 128.1, 127.1, 65.5, 65.2, 57.6, 42.6, 40.8, 30.5, 30.3, 19.0, 18.9, 13.6, 13.6; HPLC (Chiralpak AS-H, hexane/i-propanol=100/1, flow rate 1.0 mL/min, λ=254 nm): $t_{major}$=28.2 min, $t_{minor}$=29.9 min, ee=96%; $[\alpha]^{22}_D$=+19.65 (c=1.0 in CHCl$_3$); ESI-HRMS (m/z) calcd. for C$_{26}$H$_{32}$O$_5$Na ((M+Na)$^+$): 447.2147, found: 447.2145, calcd. for C26H33O5 ((M+H)$^+$): 425.2328, found: 425.2316.

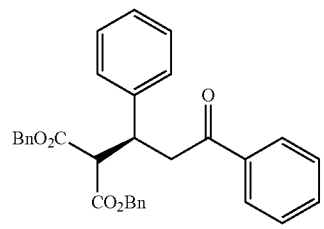

3fa

Dibenzyl 2-(3-oxo-1,3-diphenylpropyl)malonate11 (table 2, entry 9)

It was synthesized in accordance with the above-mentioned manipulation.

Yield 85%, White solid, Mp 89-92° C.; IR [cm$^{-1}$] (KBr): 1735, 1682, 1230, 1154; $^1$H NMR (600.2 MHz, CDCl$_3$, TMS): δ=7.82-7.77 (m, 2H; Ar), 7.52-7.47 (m, 1H; Ar), 7.39-7.35 (m, 2H; Ar), 7.29-7.13 (m, 13H; Ar), 7.07-7.04 (m, 2H; Ar), 5.18-5.09 (m, 2H; OCH$_2$), 4.90 (s, 2H; OCH$_2$), 4.25-4.19 (m, 1H; CH), 3.97-3.92 (m, 1H; CH), 3.47-3.42 (m, 2H; CH$_2$); $^{13}$C {$^1$H} NMR (150.9 MHz, CDCl$_3$, TMS): δ=197.3, 168.0, 167.5, 140.3, 136.7, 135.1, 135.0, 133.0, 128.5, 128.4, 128.3, 128.1, 128.0, 127.2, 67.3, 67.1, 57.5, 42.2, 40.7; HPLC (Chiralpak AS-H, hexane/i-propanol=19/1, flow rate 0.5 mL/min, λ=254 nm): t$_{major}$=56.3 min, t$_{minor}$=63.7 min, ee=84%; [α]$^{21}_D$=+17.55 (c=1.0 in CHCl$_3$); ESI-HRMS (m/z) calcd. for C$_{32}$H$_{28}$O$_5$Na ((M+Na)$^+$): 515.1834, found: 515.1847.

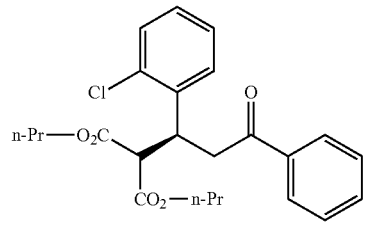

3cb

Dipropyl 2-(1-(2-chlorophenyl)-3-oxo-3-phenylpropyl)malonate (table 3, entry 1)

It was synthesized in accordance with the above-mentioned manipulation.

Yield 76%, Colorless liquid; IR [cm$^{-1}$] (neat): 1730, 1687, 1266, 1227, 1160, 738; $^1$H NMR (600.2 MHz, CDCl$_3$, TMS): δ=7.94-7.90 (m, 2H; Ar), 7.54-7.49 (m, 1H; Ar), 7.41 (appearance of br t, $^3$J$_{HH}$=7.8 Hz, 2H; Ar), 7.34-7.30 (m, 2H; Ar), 7.16-7.09 (m, 2H; Ar), 4.66 (t d, $^3$J$_{HH}$=8.8, $^3$J$_{HH}$=4.3 Hz, 1H; CH), 4.13-4.00 (m, 3H; CH, OCH$_2$), 3.94 (t, $^3$J$_{HH}$=6.7 Hz, 2H; OCH$_2$), ABM spin system (A=B=M=H, δ$_A$=3.71, δ$_B$=3.62, $^2$J$_{AB}$=17.2, $^3$J$_{AM}$=9.1, $^3$J$_{BM}$=4.3 Hz, 2H; CH$_2$), 1.63-1.45 (m, 4H; CH$_2$CH$_3$), 0.86 (t, $^3$J$_{HH}$=7.3 Hz, 3H; CH$_3$), 0.83 (t, $^3$J$_{HH}$=7.5 Hz, 3H; CH$_3$); $^{13}$C {$^1$H} NMR (150.9 MHz, CDCl$_3$, TMS): δ=197.5, 168.4, 167.9, 137.9, 136.8, 134.1, 133.1, 130.1, 129.4, 128.5, 128.2, 128.1, 126.8, 67.1, 67.1, 55.2, 40.3, 37.4, 21.8, 21.7, 10.2, 10.2; HPLC (Chiracel OJ-H, hexane/i-propanol=9/1, flow rate 0.5 mL/min, λ=254 nm): t$_{major}$=20.5 min, t$_{minor}$=26.6 min, ee=92%; [α]$^{22}_D$=+41.20 (c=1.0 in CHCl$_3$), ESI-HRMS (m/z) calcd. for C$_{24}$H$_{27}$ClO$_5$Na ((M+Na)$^+$): 453.1445, found: 453.1437.

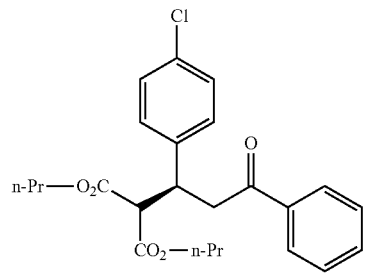

3cc

Dipropyl 2-(1-(4-chlorophenyl)-3-oxo-3-phenylpropyl)malonate (table 3, entry 2)

It was synthesized in accordance with the above-mentioned manipulation.

Yield 93%, White solid, Mp 91-94° C.; IR [cm$^{-1}$] (KBr): 1727, 1686, 1239; $^1$H NMR (600.2 MHz, CDCl$_3$, TMS): δ=7.88 (br d, $^3$J$_{HH}$=7.2 Hz, 2H; Ar), 7.52 (appearance of br t, $^3$J$_{HH}$=7.3 Hz, 1H; Ar), 7.41 (t, $^3$J$_{HH}$=7.8 Hz, 2H; Ar), 7.23-7.19 (m, 4H; Ar), 4.19-4.05 (m, 3H; CH, OCH$_2$), 3.88 (t, $^3$J$_{HH}$=6.6 Hz, 2H; OCH$_2$), 3.82 (d, $^3$J$_{HH}$=9.5 Hz, 1H; CH), ABM spin system (A=B=M=H, δ$_A$=3.53, δ$_B$=3.45, $^2$J$_{AB}$=17.0, $^3$J$_{AM}$=4.2, $^3$J$_{BM}$=9.5 Hz, 2H; CH$_2$), 1.64 (appearance of sext, $^3$J$_{HH}$=7.2 Hz, 2H; CH$_2$CH$_3$), 1.50-1.41 (m, 2H; CH$_2$CH$_3$), 0.90 (t, $^3$J$_{HH}$=7.3 Hz, 3H; CH$_3$), 0.79 (t, $^3$J$_{HH}$=7.5 Hz, 3H; CH$_3$); $^{13}$C {$^1$H} NMR (150.9 MHz, CDCl$_3$, TMS): δ=197.3, 168.2, 167.7, 139.1, 136.7, 133.2, 132.9, 129.7, 128.6, 128.5, 128.0, 67.3, 67.1, 57.4, 42.4, 40.2, 21.8, 21.7, 10.3, 10.2; HPLC (Chiracel OJ-H, hexane/i-propanol=19/1, flow rate 0.3 mL/min, λ=254 nm): t$_{major}$=47.8 min, t$_{minor}$=54.8 min, ee=97%; [α]$^{22}_D$=+24.09 (c=1.0 in CHCl$_3$); ESI-HRMS (m/z) calcd. for C$_{24}$H$_{27}$ClO$_5$Na ((M+Na)$^+$): 453.1445, found: 453.1486.

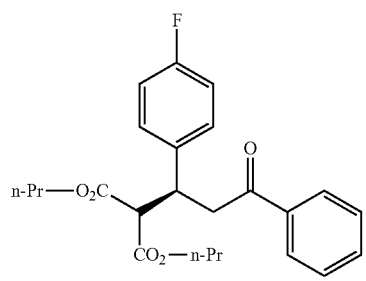

3cd

Dipropyl 2-(1-(4-fluorophenyl)-3-oxo-3-phenylpropyl)malonate (table 3, entry 3)

It was synthesized in accordance with the above-mentioned manipulation.

Yield 92%, White solid, Mp 35-38° C.; IR [cm$^{-1}$] (neat): 1733, 1687, 1510, 1226, 1161, 739; $^1$H NMR (600.2 MHz, CDCl$_3$, TMS): δ=7.91-7.87 (m, 2H; Ar), 7.52 (appearance of br t, $^3$J$_{HH}$=7.5 Hz, 1H; Ar), 7.42 (t, $^3$J$_{HH}$=7.8 Hz, 2H; Ar), 7.27-7.23 (m, 2H; Ar), 6.92 (appearance of br t, $^3$J$_{HH}$=8.7 Hz, 2H; Ar), 4.20-4.06 (m, 3H; CH, OCH$_2$), 3.87 (t, $^3$J$_{HH}$=6.8 Hz, 2H; OCH$_2$), 3.82 (d, $^3$J$_{HH}$=9.6 Hz, 1H; CH), ABM spin system (A=B=M=H, $\delta_A$=3.53, $\delta_B$=3.44, $^2J_{AB}$=16.6, $^3J_{AM}$=4.3, $^3J_{BM}$=9.6 Hz, 2H; CH$_2$), 1.64 (appearance of sext, $^3J_{HH}$=7.0 Hz, 2H; CH$_2$CH$_3$), 1.50-1.40 (m, 2H; CH$_2$CH$_3$), 0.91 (t, $^3J_{HH}$=7.5 Hz, 3H; CH$_3$), 0.79 (t, $^3J_{HH}$=7.5 Hz, 3H; CH$_3$); $^{13}$C {$^1$H} NMR (150.9 MHz, CDCl$_3$, TMS): δ=197.4, 168.3, 167.8, 161.8 (d, J$_{CF}$=245.4 Hz), 136.8, 136.3, 133.1, 129.9 (d, J$_{CF}$=7.9 Hz), 128.6, 128.1, 115.2 (d, J$_{CF}$=21.2 Hz), 67.3, 67.0, 57.6, 42.6, 40.1, 21.8, 21.7, 10.3, 10.2; HPLC (Chiracel OJ-H, hexane/i-propanol=19/1, flow rate 0.3 mL/min, λ=254 nm): t$_{major}$=50.7 min, t$_{minor}$=63.1 min, ee=98%; [α]$^{21}_D$=+25.21 (c=1.0 in CHCl$_3$); ESI-HRMS (m/z) calcd. for C$_{24}$H$_{27}$FO$_5$Na ((M+Na)$^+$): 437.1740, found: 437.1728.

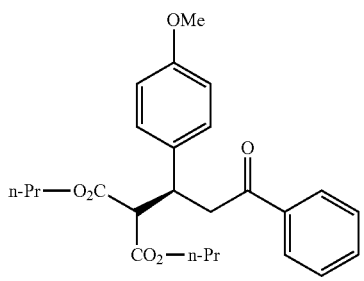

Dipropyl 2-(1-(4-methoxyphenyl)-3-oxo-3-phenylpropyl)malonate (table 3, entry 4)

It was synthesized in accordance with the above-mentioned manipulation.

Yield 80%, White solid, Mp 41-44° C.; IR [cm$^{-1}$] (KBr): 1729, 1678, 1511, 1243, 1162; $^1$H NMR (600.2 MHz, CDCl$_3$, TMS): δ=7.89 (br d, $^3J_{HH}$=7.1 Hz, 2H; Ar), 7.50 (appearance of br t, $^3J_{HH}$=7.5 Hz, 1H; Ar), 7.40 (t, $^3J_{HH}$=7.8 Hz, 2H; Ar), 7.17 (d, $^3J_{HH}$=8.7 Hz, 2H; Ar), 6.76 (d, $^3J_{HH}$=8.5 Hz, 2H; Ar), 4.16-4.05 (m, 3H; CH, OCH$_2$), 3.86 (t, $^3J_{HH}$=6.6 Hz, 2H; OCH$_2$), 3.82 (d, $^3J_{HH}$=9.6 Hz, 1H; CH), 3.72 (s, 3H; OCH$_3$), ABM spin system (A=B=M=H, $\delta_A$=3.51, $\delta_B$=3.42, $^2J_{AB}$=16.5, $^3J_{AM}$=4.2, $^3J_{BM}$=9.5 Hz, 2H; CH$_2$), 1.64 (appearance of next, $^3J_{HH}$=7.1 Hz, 2H; CH$_2$CH$_3$), 1.50-1.40 (m, 2H; CH$_2$CH$_3$), 0.91 (t, $^3J_{HH}$=7.5 Hz, 3H; CH$_3$), 0.79 (t, $^3J_{HH}$=7.5 Hz, 3H; CH$_3$); $^{13}$C {$^1$H} NMR (150.9 MHz, CDCl$_3$, TMS): δ=197.7, 168.5, 167.9, 158.6, 136.9, 133.0, 132.5, 129.2, 128.5, 128.1, 113.8, 67.2, 66.9, 57.8, 55.1, 42.8, 40.2, 21.8, 21.7, 10.3, 10.2; HPLC (Chiracel OJ-H, hexane/i-propanol=9/1, flow rate 1.5 mL/min, λ=254 nm): t$_{major}$=17.6 min, t$_{minor}$=11.0 min, ee>99%; [α]$^{21}_D$=+17.51 (c=1.0 in CHCl$_3$); ESI-HRMS (m/z) calcd. for C$_{25}$H$_{30}$O$_6$Na ((M+Na)$^+$): 449.1940, found: 449.1939.

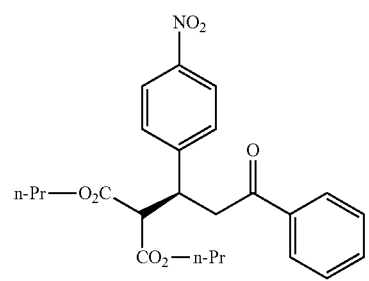

Dipropyl 2-(1-(4-nitrophenyl)-3-oxo-3-phenylpropyl)malonate (table 3, entry 5)

It was synthesized in accordance with the above-mentioned manipulation.

Yield 98%, White solid, Mp 82-86° C.; IR [cm$^{-1}$] (KBr): 1726, 1686, 1519, 1346, 1239, 1151; $^1$H NMR (600.2 MHz, CDCl$_3$, TMS): δ=8.12-8.09 (m, 2H; Ar), 7.90-7.87 (m, 2H; Ar), 7.56-7.49 (m, 3H; Ar), 7.45-7.41 (m, 2H; Ar), 4.31 (t d, $^3J_{HH}$=4.3, $^3J_{HH}$=9.4 Hz, 1H; CH), 4.17-4.07 (m, 2H; OCH$_2$), 3.93-3.86 (m, 3H; CH, OCH$_2$), ABM spin system (A=B=M=H, $\delta_A$=3.61, $\delta_B$=3.55, $^2J_{AB}$=17.3, $^3J_{AM}$=4.2, $^3J_{BM}$=9.5 Hz, 2H; CH$_2$), 1.64 (appearance of sext, $^3J_{HH}$=7.0 Hz, 2H; CH$_2$CH$_3$), 1.52-1.43 (m, 2H; CH$_2$CH$_3$), 0.91 (t, $^3J_{HH}$=7.3 Hz, 3H; CH$_3$), 0.80 (t, $^3J_{HH}$=7.4 Hz, 3H; CH$_3$); $^{13}$C {$^1$H} NMR (150.9 MHz, CDCl$_3$, TMS): δ=196.8, 167.9, 167.4, 148.6, 147.0, 136.5, 133.4, 129.4, 128.7, 128.0, 123.6, 67.5, 67.3, 56.9, 42.0, 40.4, 21.8, 21.7, 10.2, 10.2; HPLC (Chiracel OJ-H, hexane/i-propanol=9/1, flow rate 1.0 mL/min, λ=254 nm): t$_{major}$=28.5 min, t$_{minor}$=41.2 min, ee=96%; [α]$^{22}_D$=+31.37 (c=1.0 in CHCl$_3$); ESI-HRMS (m/z) calcd. for C$_{24}$H$_{27}$NO$_7$Na ((M+Na)$^+$): 464.1685, found: 464.1644.

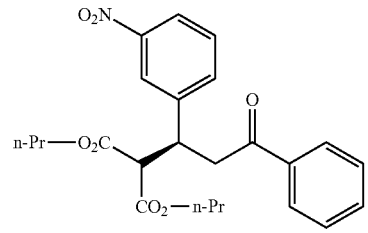

Dipropyl 2-(1-(3-nitrophenyl)-3-oxo-3-phenylpropyl)malonate (table 3, entry 6)

It was synthesized in accordance with the above-mentioned manipulation.

Yield 94%, Colorless liquid; IR [cm$^{-1}$] (neat): 1731, 1686, 1638, 1532, 1352, 1265, 738; $^1$H NMR (600.2 MHz, CDCl$_3$, TMS): δ=8.18 (t, J$_{HH}$=1.9 Hz, 1H; Ar), 8.04 (d d, J$_{HH}$=1.8 Hz, J$_{HH}$=8.2 Hz, 1H; Ar), 7.89 (br d, J$_{HH}$=7.2 Hz, 2H; Ar), 7.71 (br d, J$_{HH}$=7.8 Hz, 1H; Ar), 7.54 ((br t, J$_{HH}$=7.3 Hz, 1H; Ar), 7.46-7.41 (m, 3H; Ar), 4.32 (t d, $^3J_{HH}$=4.3, $^3J_{HH}$=9.3 Hz, 1H; CH), 4.17-4.08 (m, 2H; OCH$_2$), 3.92-3.88 (m, 3H; CH, OCH$_2$), ABM spin system (A=B=M=H, $\delta_A$=3.63, $\delta_B$=3.57, $^2J_{AB}$=17.4, $^3J_{AM}$=4.4, $^3J_{BM}$=9.4 Hz, 2H; CH$_2$), 1.64 (appearance of sext, $^3J_{HH}$=7.1 Hz, 2H; CH$_2$CH$_3$), 1.52-1.41 (m, 2H; CH$_2$CH$_3$), 0.91 (t, $^3J_{HH}$=7.5 Hz, 3H; CH$_3$), 0.79 (t, $^3J_{HH}$=7.4

Hz, 3H; CH$_3$); $^{13}$C {$^1$H} NMR (150.9 MHz, CDCl$_3$, TMS): δ=196.9, 168.0, 167.5, 148.2, 143.1, 136.5, 135.3, 133.4, 129.3, 128.7, 128.0, 123.1, 122.2, 67.5, 67.2, 57.0, 42.1, 40.2, 21.8, 21.7, 10.2, 10.1; HPLC (Chiralpak AD-H, hexane/i-propanol=9/1, flow rate 1.0 mL/min, λ=254 nm): t$_{major}$=48.9 min, t$_{minor}$=32.1 min, ee=94%; [α]$^{23}_D$=+31.81 (c=1.0 in CHCl$_3$); ESI-HRMS (m/z) calcd. for C$_{24}$H$_{27}$NO$_7$Na ((M+Na)$^+$): 464.1685, found: 464.1658.

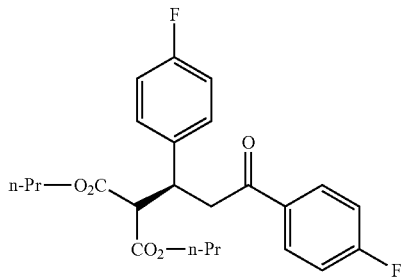

3ch

Dipropyl 2-(1,3-bis(4-fluorophenyl)-3-oxopropyl)malonate (table 3, entry 7)

It was synthesized in accordance with the above-mentioned manipulation.

Yield 91%, Colorless liquid; IR [cm$^{-1}$] (neat): 1732, 1686, 1600, 1510, 1228, 1157; $^1$H NMR (600.2 MHz, CDCl$_3$, TMS): δ=7.94-7.91 (m, 2H; Ar), 7.26-7.22 (m, 2H; Ar), 7.11-7.06 (m, 2H; Ar), 6.95-6.90 (m, 2H; Ar), 4.18-4.06 (m, 3H; CH, OCH$_2$), 3.86 (t, $^3J_{HH}$=6.6 Hz, 2H; OCH$_2$), 3.81 (d, $^3J_{HH}$=9.6 Hz, 1H; CH), 3.72 (s, 3H; OCH$_3$), ABM spin system (A=B=M=H, δ$_A$=3.50, δ$_B$=3.38, $^2J_{AB}$=16.4, $^3J_{AM}$=4.2, $^3J_{BM}$=9.6 Hz, 2H; CH$_2$), 1.64 (appearance of sext, $^3J_{HH}$=7.1 Hz, 2H; CH$_2$CH$_3$), 1.50-1.40 (m, 2H; CH$_2$CH$_3$), 0.91 (t, $^3J_{HH}$=7.5 Hz, 3H; CH$_3$), 0.79 (t, $^3J_{HH}$=7.4 Hz, 3H; CH$_3$); $^{13}$C {$^1$H} NMR (150.9 MHz, CDCl$_3$, TMS): δ=195.9, 168.4, 167.8, 165.8 (d, J$_{CF}$=254.7 Hz), 161.7 (d, J$_{CF}$=245.7 Hz), 136.1, 133.2, 130.8 (d, J$_{CF}$=9.0 Hz), 129.9 (d, J$_{CF}$=7.9 Hz), 115.7 (d, J$_{CF}$=21.8 Hz), 115.3 (d, J$_{CF}$=21.3 Hz), 67.3, 67.1, 57.6, 42.6, 40.2, 21.9, 21.7, 10.3, 10.2; HPLC (Chiralpak AS-H, hexane/i-propanol=9/1, flow rate 0.5 mL/min, λ=254 nm): t$_{major}$=20.3 min, t$_{minor}$=23.4 min, ee=96%; [α]$^{22}_D$=+21.56 (c=1.0 in CHCl$_3$); ESI-HRMS (m/z) calcd. for C$_{24}$H$_{26}$F$_2$O$_5$Na ((M+Na)$^+$): 455.1646, found: 455.1668.

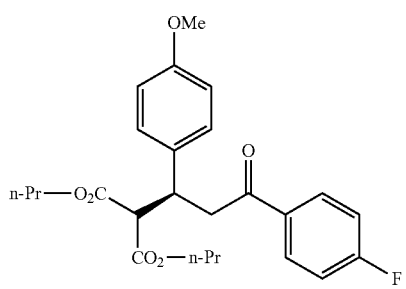

3ci

Dipropyl 2-(3-(4-fluorophenyl)-1-(4-methoxyphenyl)-3-oxopropyl)malonate (table 3, entry 8)

It was synthesized in accordance with the above-mentioned manipulation.

Yield 81%, White solid, Mp 60-63° C.; IR [cm$^{-1}$] (neat): 1731, 1686, 1599, 1514, 1266, 1251, 1157, 739; $^1$H NMR (600.2 MHz, CDCl$_3$, TMS): δ=7.94-7.91 (m, 2H; Ar), 7.18-7.15 (m, 2H; Ar), 7.07 (appearance of br t, $^3J_{HH}$=8.6 Hz, 2H; Ar), 6.78-6.75 (m, 2H; Ar), 4.15-4.05 (m, 3H; CH, OCH$_2$), 3.87 (t, $^3J_{HH}$=6.7 Hz, 2H; OCH$_2$), 3.82 (d, $^3J_{HH}$=9.6 Hz, 1H; CH), ABM spin system (A=B=M=H, δ$_A$=3.53, δ$_B$=3.40, $^2J_{AB}$=16.7, $^3J_{AM}$=4.3, $^3J_{BM}$=9.6 Hz, 2H; CH$_2$), 1.68-1.61 (m, 2H; CH$_2$CH$_3$), 1.50-1.40 (m, 2H; CH$_2$CH$_3$), 0.91 (t, $^3J_{HH}$=7.5 Hz, 3H; CH$_3$), 0.79 (t, $^3J_{HH}$=7.4 Hz, 3H; CH$_3$); $^{13}$C {$^1$H} NMR (150.9 MHz, CDCl$_3$, TMS): δ=196.2, 168.6, 167.9, 165.7 (d, J$_{CF}$=254.6 Hz), 158.6, 133.4, 132.3, 130.8 (d, J$_{CF}$=9.2 Hz), 129.2, 115.6 (d, J$_{CF}$=21.8 Hz), 113.9, 67.2, 67.0, 57.8, 55.1, 42.7, 40.3, 21.9, 21.7, 10.3, 10.2; HPLC (Chiracel OD-H, hexane/i-propanol=19/1, flow rate 0.5 mL/min, λ=254 nm): t$_{major}$=33.0 min, t$_{minor}$=29.4 min, ee>99%; [α]$^{21}_D$=+16.28 (c=1.0 in CHCl$_3$); ESI-HRMS (m/z) calcd. for C$_{25}$H$_{29}$FO$_6$Na ((M+Na)$^+$): 467.1846, found: 467.1852.

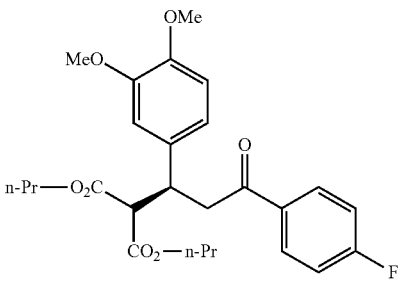

3cj

Dipropyl 2-(1-(3,4-dimethoxyphenyl)-3-(4-fluorophenyl)-3-oxopropyl)malonate (table 3, entry 9)

It was synthesized in accordance with the above-mentioned manipulation.

Yield 61%, Colorless liquid; IR [cm$^{-1}$] (neat): 1728, 1686, 1598, 1519, 1265, 746, 705; $^1$H NMR (600.2 MHz, CDCl$_3$, TMS): δ=7.95-7.91 (m, 2H; Ar), 7.11-7.06 (m, 2H; Ar), 6.79-6.72 (m, 3H; Ar), 4.16-4.05 (m, 3H; CH, OCH$_2$), 3.88 (t, $^3J_{HH}$=6.6 Hz, 2H; OCH$_2$), 3.84 (d, $^3J_{HH}$=9.6 Hz, 1H; CH), 3.82 (s, 3H; OCH$_3$), 3.80 (s, 3H; OCH$_3$), ABM spin system (A=B=M=H, δ$_A$=3.50, δ$_B$=3.39, $^2J_{AB}$=16.3, $^3J_{AM}$=4.3, $^3J_{BM}$=9.4 Hz, 2H; CH$_2$), 1.64 (appearance of sext, $^3J_{HH}$=7.1 Hz, 2H; CH$_2$CH$_3$), 1.51-1.41 (m, 2H; CH$_2$CH$_3$), 0.91 (t, $^3J_{HH}$=7.4 Hz, 3H; CH$_3$), 0.80 (t, $^3J_{HH}$=7.4 Hz, 3H; CH$_3$); $^{13}$C {$^1$H} NMR (150.9 MHz, CDCl$_3$, TMS): δ=196.3, 168.5, 167.9, 165.7 (d, J$_{CF}$=254.8 Hz), 148.7, 148.1, 133.4, 132.9, 130.8 (d, J$_{CF}$=9.2 Hz), 120.0, 115.6 (d, J$_{CF}$=21.8 Hz), 111.9, 111.2, 67.2, 67.0, 57.7, 55.9, 55.8, 42.7, 40.7, 21.9, 21.7, 10.3, 10.2; HPLC (Chiralpak AS-H, hexane/i-propanol=9/1, flow rate 1.0 mL/min, λ=254 nm): t$_{major}$=16.4 min, t$_{minor}$=14.0 min, ee=96%; [α]$^{22}_D$=+17.02 (c=0.8 in CHCl$_3$); ESI-HRMS (m/z) calcd. for C$_{26}$H$_{31}$FO$_7$Na ((M+Na)$^+$): 497.1951, found: 497.1966.

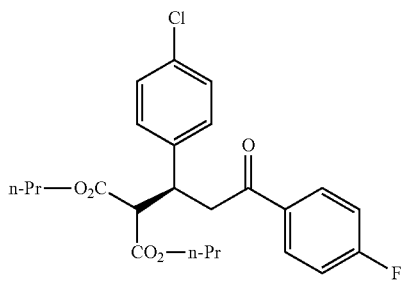

Dipropyl 2-(1-(4-chlorophenyl)-3-(4-fluorophenyl)-3-oxopropyl)malonate (table 3, entry 10)

It was synthesized in accordance with the above-mentioned manipulation.

Yield 97%, White solid, Mp 69-71° C.; IR [cm$^{-1}$] (KBr): 1730, 1685, 1600, 1300, 1238, 1157; $^1$H NMR (600.2 MHz, CDCl$_3$, TMS): δ=7.94-7.90 (m, 2H; Ar), 7.21 (br s, 4H; Ar), 7.11-7.07 (m, 2H; Ar), 4.17-4.05 (m, 3H; CH, OCH$_2$), 3.88 (t, $^3J_{HH}$=6.7 Hz, 2H; OCH$_2$), 3.82 (d, $^3J_{HH}$=9.6 Hz, 1H; CH), ABM spin system (A=B=M=H, δ$_A$=3.53, δ$_B$=3.41, $^2J_{AB}$=16.6, $^3J_{AM}$=4.2, $^3J_{BM}$=9.6 Hz, 2H; CH$_2$), 1.64 (appearance of sext, $^3J_{HH}$=7.1 Hz, 2H; CH$_2$CH$_3$), 1.51-1.41 (m, 2H; CH$_2$CH$_3$), 0.91 (t, $^3J_{HH}$=7.3 Hz, 3H; CH$_3$), 0.78 (t, $^3J_{HH}$=7.5 Hz, 3H; CH$_3$); $^{13}$C {$^1$H} NMR (150.9 MHz, CDCl$_3$, TMS): δ=195.7, 168.3, 167.7, 165.8 (d, J$_{CF}$=255.0 Hz), 139.0, 133.2, 133.0, 130.8 (d, J$_{CF}$=9.1 Hz), 129.7, 128.6, 115.7 (d, J$_{CF}$=21.9 Hz), 67.3, 67.1, 57.3, 42.3, 21.8, 21.7, 10.2, 10.2; HPLC (Chiracel OD-H, hexane/i-propanol=19/1, flow rate 0.5 mL/min, λ=254 nm): t$_{major}$=22.8 min, t$_{minor}$=20.1 min, ee=97%; [α]$^{20}_D$=+20.30 (c=1.0 in CHCl$_3$); ESI-HRMS (m/z) calcd. for C$_{24}$H$_{26}$ClFO$_5$Na ((M+Na)$^+$): 471.1350, found: 471.1350.

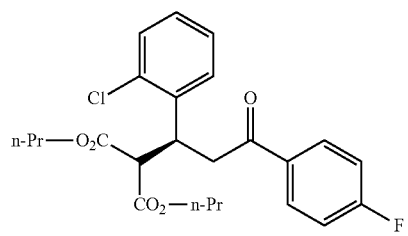

Dipropyl 2-(1-(2-chlorophenyl)-3-(4-fluorophenyl)-3-oxopropyl)malonate (table 3, entry 11)

It was synthesized in accordance with the above-mentioned manipulation.

Yield 80%, Colorless liquid; IR [cm$^{-1}$] (neat): 1732, 1686, 1599, 1265, 1232, 1156, 738, 705; $^1$H NMR (600.2 MHz, CDCl$_3$, TMS): δ=7.97-7.94 (m, 2H; Ar), 7.34-7.28 (m, 2H; Ar), 7.16-7.06 (m, 4H; Ar), 4.64 (t d, $^3J_{HH}$=5.5, $^3J_{HH}$=8.3 Hz, 1H; CH), 4.12-4.01 (m, 3H; CH, OCH$_2$), 3.94 (t, $^3J_{HH}$=6.6 Hz, 2H; OCH$_2$), ABM spin system (A=B=M=H, δ$_A$=3.64, δ$_B$=3.60, $^2J_{AB}$=16.7, $^3J_{AM}$=8.1, $^3J_{BM}$=5.1 Hz, 2H; CH$_2$), 1.60 (appearance of sext, $^3J_{HH}$=7.1 Hz, 2H; CH$_2$CH$_3$), 1.55-1.45 (m, 2H; CH$_2$CH$_3$), 0.87 (t, $^3J_{HH}$=7.3 Hz, 3H; CH$_3$), 0.83 (t, $^3J_{HH}$=7.4 Hz, 3H; CH$_3$); $^{13}$C {$^1$H} NMR (150.9 MHz, CDCl$_3$, TMS): δ=196.0, 168.4, 167.9, 165.7 (d, J$_{CF}$=254.8 Hz), 137.7, 134.1, 133.3, 130.8 (d, J$_{CF}$=9.3 Hz), 130.1, 129.3, 128.3, 126.8, 115.6 (d, J$_{CF}$=21.8 Hz), 67.2, 67.1, 55.2, 40.4, 37.5, 21.8, 21.7, 10.2, 10.2; HPLC (Chiralpak AD-H, hexane/i-propanol=9/1, flow rate 1.0 mL/min, λ=254 nm): t$_{major}$=39.9 min, t$_{minor}$=16.8 min, ee=93%; [α]$^{22}_D$=+35.13 (c=1.0 in CHCl$_3$); ESI-HRMS (m/z) calcd. for C$_{24}$H$_{26}$ClFO$_5$Na ((M+Na)$^+$): 471.1350, found: 471.1335.

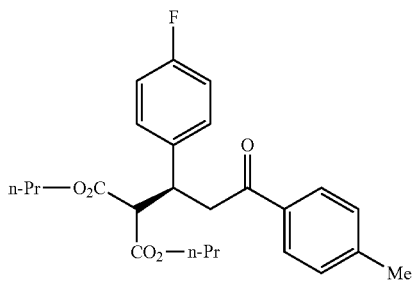

Dipropyl 2-(1-(4-fluorophenyl)-3-oxo-3-p-tolylpropyl)malonate (table 3, entry 12)

It was synthesized in accordance with the above-mentioned manipulation.

Yield 90%, White solid, Mp 64-67° C.; IR [cm$^{-1}$] (KBr): 1727, 1673, 1606, 1513, 1296, 1242, 836; $^1$H NMR (600.2 MHz, CDCl$_3$, TMS): δ=7.78 (d, $^3J_{HH}$=8.2 Hz, 2H; Ar), 7.27-7.20 (m, 4H; Ar), 6.93-6.89 (m, 2H; Ar), 4.20-4.05 (m, 3H; CH, OCH$_2$), 3.86 (t, $^3J_{HH}$=6.6 Hz, 2H; OCH$_2$), 3.82 (d, $^3J_{HH}$=9.6 Hz, 1H; CH), ABM spin system (A=B=M=H, δ$_A$=3.49, δ$_B$=3.41, $^2J_{AB}$=16.6, $^3J_{AM}$=4.2, $^3J_{BM}$=9.5 Hz, 2H; CH$_2$), 2.37 (s, 3H; CH$_3$), 1.64 (appearance of sext, $^3J_{HH}$=7.1 Hz, 2H; CH$_2$CH$_3$), 1.49-1.40 (m, 2H; CH$_2$CH$_3$), 0.91 (t, $^3J_{HH}$=7.5 Hz, 3H; CH$_3$), 0.79 (t, $^3J_{HH}$=7.4 Hz, 3H; CH$_3$); $^{13}$C {$^1$H} NMR (150.9 MHz, CDCl$_3$, TMS): δ=197.0, 168.3, 167.8, 161.8 (d, J$_{CF}$=245.3 Hz), 143.9, 136.3, 134.3, 129.9 (d, J$_{CF}$=7.6 Hz), 129.2, 128.2, 115.2 (d, J$_{CF}$=21.3 Hz), 67.2, 67.0, 57.6, 42.4, 40.2, 21.8, 21.6, 21.5, 10.2, 10.1; HPLC (Chiralpak AS-H, hexane/i-propanol=9/1, flow rate 0.5 mL/min, λ=254 nm): t$_{major}$=30.8 min, t$_{minor}$=33.5 min, ee=98%; [α]$^{21}_D$=+24.25 (c=1.0 in CHCl$_3$); ESI-HRMS (m/z) calcd. for C$_{25}$H$_{29}$FO$_5$Na ((M+Na)$^+$): 451.1897, found: 451.1859.

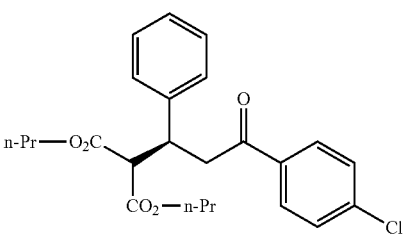

Dipropyl 2-(3-(4-chlorophenyl)-3-oxo-1-phenylpropyl)malonate (table 3, entry 13)

It was synthesized in accordance with the above-mentioned manipulation.

Yield 98%, Colorless liquid; IR [cm$^{-1}$] (neat): 1731, 1687, 1589, 1265, 743, 703; $^1$H NMR (600.2 MHz, CDCl$_3$, TMS): δ=7.84-7.81 (m, 2H; Ar), 7.39-7.36 (m, 2H; Ar), 7.26-7.21 (m, 4H; Ar), 7.17-7.14 (m, 1H; Ar), 4.18-4.05 (m, 3H; CH, OCH$_2$), 3.87-3.84 (m, 3H; CH, OCH$_2$), ABM spin system (A=B=M=H, δ$_A$=3.53, δ$_B$=3.42, $^2J_{AB}$=16.6, $^3J_{AM}$=4.4, $^3J_{BM}$=9.4 Hz, 2H; CH$_2$), 1.63 (appearance of sext, $^3J_{HH}$=7.0 Hz, 2H; CH$_2$CH$_3$), 1.47-1.38 (m, 2H; CH$_2$CH$_3$), 0.90 (t, $^3J_{HH}$=7.5 Hz, 3H; CH$_3$), 0.77 (t, $^3J_{HH}$=7.4 Hz, 3H; CH$_3$); $^{13}$C {$^1$H} NMR (150.9 MHz, CDCl$_3$, TMS): δ=196.5, 168.5, 167.8, 140.3, 139.4, 135.2, 129.6, 128.8, 128.5, 128.2, 127.2, 67.2, 67.0, 57.5, 42.6, 40.9, 21.8, 21.6, 10.3, 10.2; HPLC (2× Chiracel OJ-H, hexane/i-propanol=9/1, flow rate 0.5 mL/min, λ=254 nm): t$_{major}$=76.2 min, t$_{minor}$=68.8 min, ee=99%; [α]$^{21}_D$=+17.53 (c=1.0 in CHCl$_3$); ESI-HRMS (m/z) calcd. for C$_{24}$H$_{27}$ClO$_5$Na ((M+Na)$^+$): 453.1445, found: 453.1418.

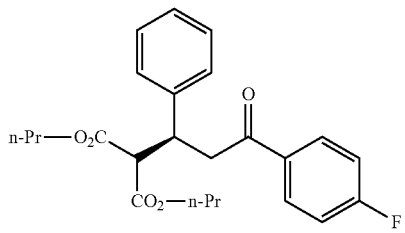

3co

Dipropyl 2-(3-(4-fluorophenyl)-3-oxo-1-phenylpropyl)malonate (table 3, entry 14)

It was synthesized in accordance with the above-mentioned manipulation.

Yield 92%, Colorless liquid; IR [cm$^{-1}$] (neat): 1731, 1686, 1599, 1265, 1157, 745, 703; $^1$H NMR (600.2 MHz, CDCl$_3$, TMS): δ=7.94-7.90 (m, 2H; Ar), 7.27-7.21 (m, 4H; Ar), 7.18-7.14 (m, 1H; Ar), 7.09-7.05 (m, 2H; Ar), 4.19-4.05 (m, 3H; CH, OCH$_2$), 3.87-3.83 (m, 3H; CH, OCH$_2$), ABM spin system (A=B=M=H, δ$_A$=3.53, δ$_B$=3.43, $^2J_{AB}$=16.5, $^3J_{AM}$=4.3, $^3J_{BM}$=9.5 Hz, 2H; CH$_2$), 1.63 (appearance of sext, $^3J_{HH}$=7.0 Hz, 2H; CH$_2$CH$_3$), 1.47-1.38 (m, 2H; CH$_2$CH$_3$), 0.90 (t, $^3J_{HH}$=7.3 Hz, 3H; CH$_3$), 0.77 (t, $^3J_{HH}$=7.3 Hz, 3H; CH$_3$); $^{13}$C {$^1$H} NMR (150.9 MHz, CDCl$_3$, TMS): δ=196.1, 168.5, 167.8, 165.7 (d, J$_{CF}$=254.5 Hz), 140.4, 133.3, 130.8 (d, J$_{CF}$=9.2 Hz), 128.5, 128.2, 127.2, 115.6 (d, J$_{CF}$=21.9 Hz), 67.2, 67.0, 57.6, 42.5, 40.9, 21.8, 21.7, 10.3, 10.2; HPLC (Chiracel OJ-H, hexane/i-propanol=19/1, flow rate 0.5 mL/min, λ=254 nm): t$_{major}$=41.0 min, t$_{minor}$=56.7 min, ee=99%; [α]$^{22}_D$=+21.69 (c=1.0 in CHCl$_3$); ESI-HRMS (m/z) calcd. for C$_{24}$H$_{27}$FO$_5$Na ((M+Na)$^+$): 437.1740, found: 437.1729.

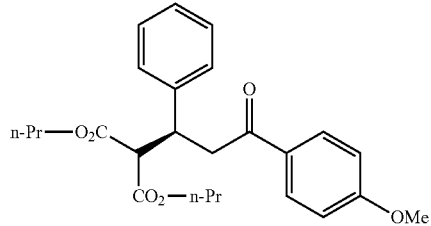

3cp

Dipropyl 2-(3-(4-methoxyphenyl)-3-oxo-1-phenylpropyl)malonate (table 3, entry 15)

It was synthesized in accordance with the above-mentioned manipulation.

Yield 85%, White solid, Mp 63-65° C.; IR [cm$^{-1}$] (neat): 1731, 1677, 1602, 1265, 1171, 739, 702; $^1$H NMR (600.2 MHz, CDCl$_3$, TMS): δ=7.89-7.86 (m, 2H; Ar), 7.27-7.20 (m, 4H; Ar), 7.16-7.12 (m, 1H; Ar), 6.89-6.86 (m, 2H; Ar), 4.17 (t d, $^3J_{HH}$=4.6, $^3J_{HH}$=9.5 Hz, 1H; CH), 4.14-4.05 (m, 2H; OCH$_2$), 3.87-3.83 (m, 3H; CH, OCH$_2$), 3.82 (s, 3H; OCH$_3$), ABM spin system (A=B=M=H, δ$_A$=3.45, δ$_B$=3.40, $^2J_{AB}$=16.3, $^3J_{AM}$=4.5, $^3J_{BM}$=9.4 Hz, 2H; CH$_2$), 1.63 (appearance of sext, $^3J_{HH}$=7.1 Hz, 2H; CH$_2$CH$_3$), 1.47-1.37 (m, 2H; CH$_2$CH$_3$), 0.90 (t, $^3J_{HH}$=7.5 Hz, 3H; CH$_3$), 0.77 (t, $^3J_{HH}$=7.4 Hz, 3H; CH$_3$); $^{13}$C {$^1$H} NMR (150.9 MHz, CDCl$_3$, TMS): δ=196.1, 168.5, 167.9, 163.4, 140.6, 130.4, 130.0, 128.4, 128.2, 127.1, 113.7, 67.2, 66.9, 57.7, 55.4, 42.3, 41.0, 21.8, 21.6, 10.3, 10.2; HPLC (Chiracel OD-H, hexane/i-propanol=19/1, flow rate 0.5 mL/min, λ=254 nm): t$_{major}$=40.4 min, t$_{minor}$=47.3 min, ee=99%; [α]$^{20}_D$=+20.73 (c=1.0 in CHCl$_3$); ESI-HRMS (m/z) calcd. for C$_{25}$H$_{30}$O$_6$Na ((M+Na)$^+$): 449.1940, found: 449.1944.

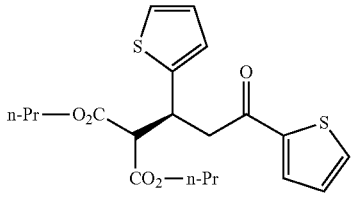

3cq

Dipropyl 2-(3-oxo-1,3-di(thiophen-2-yl)propyl)malonate (table 3, entry 16)

It was synthesized in accordance with the above-mentioned manipulation.

Yield 73%, Beige liquid; IR [cm$^{-1}$] (neat): 1734, 1663, 1416, 1265, 736, 704; $^1$H NMR (600.2 MHz, CDCl$_3$, TMS): δ=7.75-7.73 (m, 1H; Ar), 7.61-7.58 (m, 1H; Ar), 7.11-7.08 (m, 2H; Ar), 6.93-6.91 (m, 1H; Ar), 6.86-6.83 (m, 1H; Ar), 4.53-4.48 (m, 1H; CH), 4.14-4.05 (m, 2H; OCH$_2$), 3.99-3.93 (m, 2H; OCH$_2$), 3.90 (d, $^3J_{HH}$=8.4 Hz, 1H; CH), 3.48 (d, $^3J_{HH}$=6.8 Hz, 2H; CH$_2$), 1.64 (appearance of sext, $^3J_{HH}$=7.1 Hz, 2H; CH$_2$CH$_3$), 1.56-1.48 (m, 2H; CH$_2$CH$_3$), 0.91 (t, $^3J_{HH}$=7.3 Hz, 3H; CH$_3$), 0.84 (t, $^3J_{HH}$=7.3 Hz, 3H; CH$_3$); $^{13}$C {$^1$H} NMR (150.9 MHz, CDCl$_3$, TMS): δ=190.1, 168.1, 167.7, 144.1, 143.3, 133.8, 132.1, 128.1, 126.6, 125.9, 124.2, 67.3, 67.2, 57.8, 43.8, 36.3, 21.8, 21.7, 10.3, 10.2; HPLC (Chiralpak AS-H, hexane/i-propanol=9/1, flow rate 1.0 mL/min, λ=254 nm): $t_{major}$=12.7 min, $t_{minor}$=17.3 min, ee=97%; $[α]^{21}_D$=+22.21 (c=1.0 in CHCl$_3$), ESI-HRMS (m/z) calcd. for C$_{20}$H$_{24}$O$_5$S$_2$Na ((M+Na)$^+$): 431.0963, found: 431.0922.

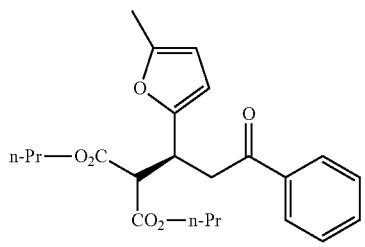

3cr

Dipropyl 2-(1-(5-methylfuran-2-yl)-3-oxo-3-phenylpropyl)malonate (table 3, entry 17)

It was synthesized in accordance with the above-mentioned manipulation.

Yield 71%, Yellow liquid; IR [cm$^{-1}$] (neat): 1735, 1686, 1265, 750; $^1$H NMR (600.2 MHz, CDCl$_3$, TMS): δ=7.95 (br d, $J_{HH}$=7.4 Hz, 2H; Ar), 7.58-7.51 (m, 1H; Ar), 7.47-7.41 (m, 2H; Ar), 5.95 (br s, 1H; Ar), 5.76 (br s, 1H; Ar), 4.29-4.23 (m, 1H; CH), 4.14-3.90 (m, 5H; CH, OCH$_2$, OCH$_2$), 3.58-3.41 (m, 2H; CH$_2$), 2.17 (s, 3H; CH$_3$), 1.68-1.53 (m, 4H; CH$_2$CH$_3$, CH$_2$CH$_3$), 0.95-0.85 (m, 6H; CH$_3$, CH$_3$); $^{13}$C {$^1$H} NMR (150.9 MHz, CDCl$_3$, TMS): δ=197.5, 168.2, 168.0, 151.6, 151.0, 136.8, 133.1, 128.5, 128.1, 107.7, 106.1, 67.1, 67.1, 55.3, 39.8, 34.4, 21.8, 21.8, 13.5, 10.3, 10.3; HPLC (Chiralpak AD-H, hexane/i-propanol=19/1, flow rate 0.5 mL/min, λ=254 nm): $t_{major}$=40.8 min, $t_{minor}$=37.2 min, ee=96%; $[α]^{21}_D$=+9.82 (c=1.0 in CHCl$_3$); ESI-HRMS (m/z) calcd. for C$_{23}$H$_{28}$O$_6$Na ((M+Na)$^+$): 423.1784, found: 423.1777.

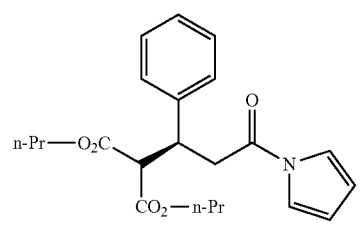

3cs

Dipropyl 2-(3-oxo-1-phenyl-3-(1H-pyrrol-1-yl)propyl)malonate (table 3, entry 18)

It was synthesized in accordance with the above-mentioned manipulation.

Yield 93%, White solid, Mp 88-91° C.; IR [cm$^{-1}$] (KBr): 1716, 1471, 1280, 1229, 1172, 748; $^1$H NMR (600.2 MHz, CDCl$_3$, TMS): δ=7.30-7.25 (m, 6H; Ar), 7.22-7.18 (m, 1H; Ar), 6.26-6.23 (m, 2H; Ar), 4.16-4.06 (m, 3H; CH, OCH$_2$), 3.88-3.84 (m, 3H; CH, OCH$_2$), ABM spin system (A=B=M=H, $δ_A$=3.45, $δ_B$=3.29, $^2J_{AB}$=16.3, $^3J_{AM}$=4.2, $^3J_{BM}$=9.7 Hz, 2H; CH$_2$), 1.64 (appearance of sext, $^3J_{HH}$=7.2 Hz, 2H; CH$_2$CH$_3$), 1.48-1.39 (m, 2H; CH$_2$CH$_3$), 0.90 (t, $^3J_{HH}$=7.5 Hz, 3H; CH$_3$), 0.78 (t, $^3J_{HH}$=7.5 Hz, 3H; CH$_3$); $^{13}$C NMR (150.9 MHz, CDCl$_3$, TMS): δ=168.3, 168.2, 167.6, 139.6, 128.6, 128.1, 127.5, 119.1, 113.1, 67.3, 67.1, 57.2, 41.1, 38.7, 21.8, 21.6, 10.2, 10.2; HPLC (Chiralpak AS-H, hexane/i-propanol=19/1, flow rate 0.5 mL/min, λ=254 nm): $t_{major}$=24.4 min, $t_{minor}$=31.2 min, ee=99%; $[α]^{20}_D$=+16.38 (c=1.0 in CHCl$_3$); ESI-HRMS (m/z) calcd. for C$_{22}$H$_{27}$NO$_5$Na ((M+Na)$^+$): 408.1787, found: 408.1755.

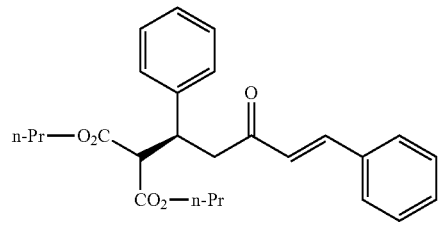

3ct

Dipropyl 2-(3-oxo-1,5-diphenylpent-4-enyl)malonate (table 3, entry 19)

It was synthesized in accordance with the above-mentioned manipulation.

Yield 75%, White solid, Mp 69-73° C.; IR [cm$^{-1}$] (KBr): 1731, 1646, 1227, 1163, 705; $^1$H NMR (600.2 MHz, CDCl$_3$, TMS): δ=7.51-7.46 (m, 3H; Ar), 7.37-7.34 (m, 3H; Ar), 7.29-7.23 (m, 4H; Ar), 7.19-7.14 (m, 1H; Ar), 7.14 (d, $^3J_{HH}$=16.4, 1H; Ar), 4.16-4.07 (m, 3H; CH, OCH$_2$), 3.87-3.81 (m, 3H; CH, OCH$_2$), ABM spin system (A=B=M=H, $δ_A$=3.20, $δ_B$=3.16, $^2J_{AB}$=16.1, $^3J_{AM}$=4.6, $^3J_{BM}$=9.2 Hz, 2H; CH$_2$), 1.65 (appearance of sext, $^3J_{HH}$=7.1 Hz, 2H; CH$_2$CH$_3$), 1.48-1.38 (m, 2H; CH$_2$CH$_3$), 0.92 (t, $^3J_{HH}$=7.5 Hz, 3H; CH$_3$), 0.77 (t, $^3J_{HH}$=7.3 Hz, 3H; CH$_3$); $^{13}$C {$^1$H} NMR (150.9 MHz, CDCl$_3$, TMS): δ=197.4, 168.4, 167.8, 142.8, 140.4, 134.5, 130.4, 128.9, 128.4, 128.3, 128.2, 127.2, 126.0, 67.2, 66.9, 57.6, 44.8, 41.0, 21.9, 21.6, 10.3, 10.2; HPLC (Chiralpak AS-H, hexane/i-propanol=9/1, flow rate 1.0 mL/min, λ=254 nm): $t_{major}$=11.8 min, $t_{minor}$=14.4 min, ee=86%; $[α]^{22}_D$=+14.56 (c=1.0 in CHCl$_3$); ESI-HRMS (m/z) calcd. for C$_{26}$H$_{30}$O$_5$Na ((M+Na)$^+$): 445.1991, found: 445.1975.

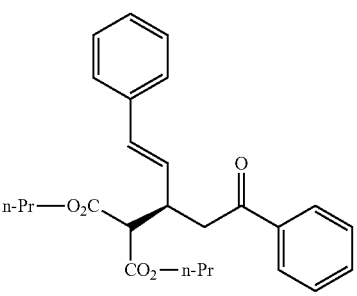

3cu

Dipropyl 2-(5-oxo-1,5-diphenylpent-1-en-3-yl)malonate (table 3, entry 20)

It was synthesized in accordance with the above-mentioned manipulation.

Yield 46%, White solid, Mp 42-45° C.; IR [cm$^{-1}$] (KBr): 1728, 1682, 1234, 754, 692; $^1$H NMR (600.2 MHz, CDCl$_3$, TMS): δ=7.98-7.94 (m, 2H; Ar), 7.56-7.52 (m, 1H; Ar), 7.47-7.43 (m, 2H; Ar), 7.29-7.22 (m, 4H; Ar), 7.20-7.16 (m, 1H; Ar), 6.46 (d, $^3J_{HH}$=15.8 Hz, 1H; Ar), 6.25 (dd, $^3J_{HH}$=15.8, $^3J_{HH}$=9.0 Hz, 1H; Ar), 4.15-4.00 (m, 4H; OCH$_2$, OCH$_2$), 3.78 (d, $^3J_{HH}$=7.5 Hz, 1H; CH), 3.73-3.67 (m, 1H; CH), ABM spin system (A=B=M=H, δ$_A$=3.40, δ$_B$=3.27, $^2J_{AB}$=16.8, $^3J_{AM}$=4.9, $^3J_{BM}$=7.9 Hz, 2H; CH$_2$), 1.68-1.55 (m, 4H; CH$_2$CH$_3$, CH$_2$CH$_3$), 0.92 (t, $^3J_{HH}$=7.5 Hz, 3H; CH$_3$), 0.87 (t, $^3J_{HH}$=7.5 Hz, 3H; CH$_3$); $^{13}$C {$^1$H} NMR (124.5 MHz, CDCl$_3$, TMS): δ=198.0, 168.4, 168.3, 137.0, 136.9, 133.1, 132.6, 128.6, 128.5, 128.4, 128.2, 127.5, 126.4, 67.1, 67.0, 55.7, 41.3, 38.8, 21.9, 21.8, 10.3, 10.3; HPLC (Chiralpak AS-H, hexane/i-propanol=40/1, flow rate 0.5 mL/min, λ=254 nm): t$_{major}$=32.5 min, t$_{minor}$=38.0 min, ee=97%; [α]$^{21}_D$=+1.20 (c=1.0 in CHCl$_3$); ESI-HRMS (m/z) calcd. for C$_{26}$H$_{30}$O$_5$Na ((M+Na)$^+$): 445.1991, found: 445.1988, C$_{26}$H$_{31}$O$_5$ ((M+H)$^+$): 423.2171, found: 423.2150.

TABLE 1

Effect of metal sources and chiral ligands.$^a$

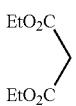

| entry | metal (×mol %) | ligand | solv. | time (h) | yield (%)$^b$ | ee (%)$^c$ |
|---|---|---|---|---|---|---|
| 1$^d$ | Ca(O-i-Pr)$_2$ (10%) | I | THF | 24 | 47 | 4 |
| 2$^d$ | Ca(O-i-Pr)$_2$ (10%) | II | THF | 24 | 47 | 49 |
| 3$^d$ | Ca(O-i-Pr)$_2$ (10%) | III | THF | 24 | 89 | 52 |
| 4$^e$ | Ca(O-i-Pr)$_2$ (5%) | III | Tol. | 18 | 58 | 65 |
| 5$^e$ | Sr(O-i-Pr)$_2$ (5%) | III | Tol. | 18 | 91 | 97 |
| 6$^e$ | Ba(O-i-Pr)$_2$ (5%) | III | Tol. | 18 | 80 | 76 |
| 7$^e$ | Ba(O-t-Bu)$_2$ (5%) | III | Tol. | 18 | 82 | 70 |

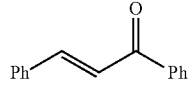

II R = 4-tolyl
III R = 2,5-dimethylbenzene

TABLE 2

Conjugate addition reactions of malonates 1a-1f to 2a.$^a$

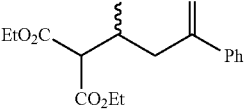

| entry | Sr(O-i-Pr)$_2$ (×mol %) | R | time (h) | yield (%)$^b$ | ee (%)$^c$ (configuration) |
|---|---|---|---|---|---|
| 1 | 5 | Me | 24 | 65 | 94 (R)$^d$ |
| 2 | 5 | Et | 18 | 91 | 97 (R)$^d$ |
| 3 | 5 | n-Pr | 7 | 92 | 99 |
| 4 | 2.5 | n-Pr | 7 | 90 | 99 |
| 5$^e$ | 1 | n-Pr | 9 | 70 | 97 |
| 6$^f$ | 0.5 | n-Pr | 24 | 72 | 97 |
| 7 | 5 | i-Pr | 21 | 83 | 89 |
| 8 | 5 | n-Bu | 3 | 85 | 96 |
| 9 | 5 | Bn | 18 | 85 | 84 |

TABLE 3

Conjugate addition reactions of 1c to enones 2b-u.[a]

n-PrO$_2$C–CH(CO$_2$-n-Pr) + R$^1$CH=CHC(O)R$^2$ → [Sr(O-i-Pr)$_2$ (5 mol %), Ligand III (6 mol %), MS 4A (100 mg), 7 h, 25°C., Toluene, 0.1M] → 3cb-cu

| entry | R$^1$ | R$^2$ | adduct | yield (%)[b] | ee (%)[c] |
|---|---|---|---|---|---|
| 1 | 2-ClC$_6$H$_4$ | Ph | 3cb | 76 | 92 |
| 2 | 4-ClC$_6$H$_4$ | Ph | 3cc | 93 | 97 |
| 3 | 4-FC$_6$H$_4$ | Ph | 3cd | 92 | 98 |
| 4 | 4-MeOC$_6$H$_4$ | Ph | 3ce | 80 | >99 |
| 5 | 4-NO$_2$C$_6$H$_4$ | Ph | 3cf | 98 | 96 |
| 6 | 3-NO$_2$C$_6$H$_4$ | Ph | 3cg | 94 | 94 |
| 7 | 4-FC$_6$H$_4$ | 4-FC$_6$H$_4$ | 3ch | 91 | 96 |
| 8 | 4-MeOC$_6$H$_4$ | 4-FC$_6$H$_4$ | 3ci | 81 | >99 |
| 9 | 3,4-di-MeOC$_6$H$_3$ | 4-FC$_6$H$_4$ | 3cj | 61 | 96 |
| 10 | 4-ClC$_6$H$_4$ | 4-FC$_6$H$_4$ | 3ck | 97 | 97 |
| 11 | 2-ClC$_6$H$_4$ | 4-FC$_6$H$_4$ | 3cl | 80 | 93 |
| 12 | 4-FC$_6$H$_4$ | 4-MeC$_6$H$_4$ | 3cm | 90 | 98 |
| 13 | Ph | 4-ClC$_6$H$_4$ | 3cn | 98 | 99 |
| 14 | Ph | 4-FC$_6$H$_4$ | 3co | 92 | 99 |
| 15 | Ph | 4-MeOC$_6$H$_4$ | 3cp | 85 | 99 |
| 16 | 2-thienyl | 2-thienyl | 3cq | 73 | 97 |
| 17[d] | 5-methylfuran-2-yl | Ph | 3cr | 71 | 96 |
| 18[e] | Ph | 1-pyrrolyl | 3cs | 90 | >99 |
| 19[f] | Ph | —CH=CHPh | 3ct | 97 | 86 |
| 20[f] | —CH=CH—Ph | Ph | 3cu | 62 | 97 |

[a]See footnote in Table 1.
[b]Isolated yields.
[c]Determined by chiral HPLC analysis.
[d]Reaction time 48 h.
[e]Reaction time 24 h.
[f]2.2 equivalents of malonate 1c were used.

[Michael Addition to Chalcone of a Malonic Ester]

0.015 mmol of strontium hexamethyldisilazide (Sr(HMDS)$_2$), 0.015 mmol of ligand, and 100 mg of molecular sieve 4A were suspended in 1 mL of toluene, and stirred for two hours at room temperature under an argon atmosphere. Thereafter, a toluene solution (1 mL) of 0.36 mmol of a malonic acid di-n-propyl ester, and a toluene solution of chalcone (0.3 mmol) were added. After the finishing of the reaction (the finishing of the reaction was confirmed by the thin-layer chromatography), a saturated ammonium chloride aqueous solution was added to the reaction solution. In addition, an organic phase was separated with dichloromethane. And a water phase was extracted with dichloromethane. The organic phase was collected and dried over anhydrous sodium sulfate. Thereafter, sodium sulfate was filtered off, and the solvent was removed by the distillation under reduced pressure. And the crude refined product was refined with the preparative thin-layer chromatography.

An enantiometric excess of the target product (refined product) obtained in such a manner was determined with a high performance liquid chromatography.

Additionally, Sr(HMDS)$_2$ was synthesized with the method (Inorg. Chem., 1991, 30, 96-101) reported by Wasterhausen. Ligand was synthesized with method (J. Am. Chem. Soc., 1997, 119, 6452-6453) reported by Evans. Chalcones were procured from TOKYO CHEMICAL INDUSTRY CO., LTD. and Wako Pure Chemical industries, LTD.

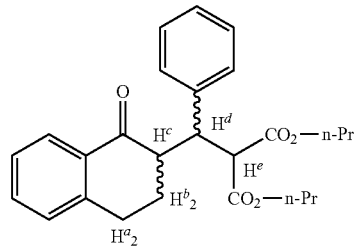

Dipropyl 2-((1-oxo-1,2,3,4-tetrahydronaphthalen-2-yl)(phenyl)methyl)malonate (table 5): Colorless oil; IR [cm$^{-1}$] (neat): 1747, 1731, 1682, 1600, 1455, 1266, 1221, 1155, 1059, 743, 702; NMR (600.2 MHz, CDCl$_3$, TMS): δ=8.01-7.97 (m, 1H; Ar), 7.41-7.37 (m, 1H; Ar), 7.32-7.11 (m, 7H; Ar), 4.98 (d, $^3J_{HH}$=12.0 Hz, 1H; CH$^c$), 4.14-4.00 (m, 2H; OCH$_2$), 3.85-3.75 (m, 3H; CH$^d$, OCH$_2$), 3.11 (dt, $^3J_{HH}$=12.9, $^3J_{HH}$=4.1 Hz, 1H; CH$^C$), 2.99-2.92 (m, 1H; CH$^a$), 2.86-2.81 (m, 1H; CH$^a$), 2.15-2.10 (m, 1H; CH$^b$), 1.86 (appearance q d, $^3J_{HH}$=12.9, J$_{HH}$=4.2 Hz, 1H; CH$^b$), 1.60 (appearance of sext, $^3J_{HH}$=7.1 Hz, 2H; CH$_2$CH$_3$), 1.40-1.32 (m, 2H; CH$_2$CH$_3$), 0.89 (t, $^3J_{HH}$=7.3 Hz, 3H; CH$_3$), 0.74 (t, $^3J_{HH}$=7.5 Hz, 3H; CH$_3$); $^{13}$C{$^1$H} NMR (150.9 MHz, CDCl$_3$, TMS): δ=198.8, 169.2, 168.7, 143.6, 139.3, 133.3, 133.2, 129.5, 128.4, 128.2, 127.3, 127.0, 126.5, 67.0, 66.7, 54.9, 49.6, 47.7, 29.5, 27.8, 21.8, 21.6, 10.2, 10.2; HPLC (Chiralpak AS-H, hexane/i-propanol=40/1, flow rate 0.5 mL/min, λ=254 nm): $t_{major}$=16.5 min, $t_{minor}$=19.6 min, ee=96%, $t_{major}$=23.3 min, $t_{minor}$=26.3 min; [α]$^{21}_D$=59.52 (c=1.0 in CHCl$_3$); ESI-HRMS (m/z) calcd. for C$_{26}$H$_{30}$O$_5$Na [(M+Na)$^+$]: 445.1991, found: 445.2042.

TABLE 4

| Strontiums | Catalyst amount (mole %) | Yield (%)[a] | Enantiometric excess (%)[b] |
|---|---|---|---|
| 1 Sr(O-i-Pr)$_2$ | 5 | 92 | 99 |
| 2 Sr(HMDS)$_2$ | 5 | 97 | 99 |
| 3 Sr(HMDS)$_2$ | 3 | 99 | 96 |
| 4 Sr(HMDS)$_2$ | 2 | 96 | 96 |

[a]Isolated yield
[b]Determined with chiral HPLC analysis

TABLE 5

| Strontiums | Compound 1 (y equivalents) | Yield (%)[a] | Diastereomer ratio | Enantiometric excess (%)[b] |
|---|---|---|---|---|
| 1 Sr(O-i-Pr)$_2$ | 2.5 | 50 | 97:3 | 80 |
| 2 Sr(O-i-Pr)$_2$ | 5 | 92 | 97:3 | 66 |
| 3 Sr(O-i-Pr)$_2$ | 1.2 | 40 | 97:3 | 88 |
| 4 Sr(HMDS)$_2$ | 1.2 | 38 | 97:3 | 95 |
| 5 Sr(HMDS)$_2$ | 1.2 | 26 | 98:2 | 95 |
| 6 Sr(HMDS)$_2$ | 2.5 | 50 | 97:3 | 94 |
| 7 Sr(HMDS)$_2$ | 1.2 | 86 | 98:2 | 60 |

[a]Isolated yield
[b]Determined with chiral HPLC analysis

TABLE 6

| Entry | Substituent R$^1$ | Substituent R$^2$ | Reaction time (time) | Yield (%)[a] | Enantioselectivity (%)[b] |
|---|---|---|---|---|---|
| 1 | 2-Cl—C$_6$H$_4$ | Ph | 7 | 82 | 95 |
| 2 | 4-Cl—C$_6$H$_4$ | Ph | 7 | 93 | 97 |
| 3 | 2-Cl—C$_6$H$_4$ | 4-F—C$_6$H$_4$ | 7 | 92 | 93 |
| 4 | Ph | —CH═CHPh | 7 | 95 | 90 |
| 5 | 4-F—C$_6$H$_4$ | 4-F—C$_6$H$_4$ | 7 | 94 | 96 |

TABLE 6-continued

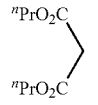

| Entry | Substituent R[1] | Substituent R[2] | Reaction time (time) | Yield (%)[a] | Enantioselectivity (%)[b] |
|---|---|---|---|---|---|
| 6 | 3-NO$_2$—C$_6$H$_4$ | Ph | 7 | 86 | 96 |
| 7 | 4-NO$_2$—C$_6$H$_4$ | Ph | 7 | 81 | 97 |

[a]Isolated yield
[b]Determined with chiral HPLC analysis

The invention claimed is:

1. A reaction method, comprising reacting a compound represented by formula [II] with a compound represented by formula [III] in the presence of a catalyst configured using MX$_2$ and a compound represented by formula [I], to form a compound of formula [IV]:

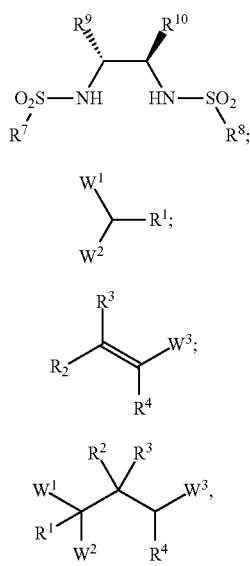

wherein:

R$^1$, R$^2$, R$^3$ and R$^4$ individually represent a H or a hydrocarbon;

W$^1$, W$^2$ and W$^3$ individually represent an electron-withdrawing group selected from the group consisting of an ester group, a carboxyl group, a carbonyl group, a nitrile group and a nitro group;

M is Sr;

X is an alkoxide group, an amide group, or a hexamethyldisilazide group; and

R$^7$, R$^8$, R$^9$, and R$^{10}$ each represents a substituted cyclic group or a unsubstituted cyclic group and wherein optionally R$^9$ and R$^{10}$ form a ring.

2. A reaction method according to claim 1, wherein said MX$_2$ is M(OR$^5$)$_2$ wherein M is Sr and R$^5$ is an alkyl group.

3. A reaction method according to claim 1, wherein said MX$_2$ is Sr(OR$^5$)$_2$ and R$^5$ is an alkyl group having a carbon number of 1 to 10.

4. A reaction method according to claim 1, wherein said X is an amide group.

5. A reaction method according to claim 1, wherein said X is hexamethyldisilazide.

6. A reaction method according to claim 1, wherein said cyclic group is an aromatic group.

7. A reaction method according to claim 1, wherein the compound represented by said general formula [I] and M of said compound MX$_2$ are coordinate-bonded to each other.

8. A reaction method according to claim 1, wherein said electron-withdrawing group is an ester group or a carbonyl group.

9. A reaction method according to claim 1, wherein the compound represented by said general formula [II] is a dicarboxylate ester.

10. A reaction method according to claim 1, wherein the compound represented by said general formula [II] is a malonic ester.

11. A reaction method according to claim 1, wherein the compound represented by said general formula [III] is an enone.

12. A reaction method according to claim 1, wherein an aromatic hydrocarbon solvent is used as a solvent of said reaction.

* * * * *